United States Patent
Holsten et al.

(10) Patent No.: US 11,529,169 B2
(45) Date of Patent: Dec. 20, 2022

(54) OPTICAL TROCAR VISUALIZATION SYSTEM AND APPARATUS

(71) Applicant: Covidien LP, Mansfield, MA (US)

(72) Inventors: Henry E. Holsten, Hamden, CT (US); Christopher K. Evans, Southington, CT (US); Robert C. Smith, Chaplin, SC (US)

(73) Assignee: Covidien LP, Mansfield, MA (US)

( * ) Notice: Subject to any disclaimer, the term of this patent is extended or adjusted under 35 U.S.C. 154(b) by 322 days.

(21) Appl. No.: 16/816,474

(22) Filed: Mar. 12, 2020

(65) Prior Publication Data
US 2020/0246043 A1 Aug. 6, 2020

Related U.S. Application Data

(63) Continuation of application No. 16/034,745, filed on Jul. 13, 2018, now Pat. No. 10,588,662, which is a (Continued)

(51) Int. Cl.
*A61B 17/34* (2006.01)
*A61M 39/06* (2006.01)
(Continued)

(52) U.S. Cl.
CPC ...... *A61B 17/3423* (2013.01); *A61B 17/0218* (2013.01); *A61B 17/3462* (2013.01); (Continued)

(58) Field of Classification Search
CPC ............ A61B 17/0218; A61B 17/3423; A61B 17/3462; A61B 2017/00862; (Continued)

(56) References Cited

U.S. PATENT DOCUMENTS

| 4,402,683 | A | 9/1983 | Kopman |
| 4,619,643 | A | 10/1986 | Bai |

(Continued)

FOREIGN PATENT DOCUMENTS

| CN | 202313634 U | 7/2012 |
| DE | 202008009527 U1 | 10/2008 |

(Continued)

OTHER PUBLICATIONS

International Search Report for (PCT/US2013/061831) date of completion is Jan. 15, 2014 (2 pages).

(Continued)

*Primary Examiner* — Nicholas J Plionis
(74) *Attorney, Agent, or Firm* — Carter, DeLuca & Farrell LLP

(57) ABSTRACT

A seal assembly including a septum seal, a lower seal support, an upper seal support and a return spring is disclosed. The septum seal includes an orifice and a plurality of apertures. The lower seal support includes an engagement surface configured to engage a portion of the septum seal. The upper seal support includes a plurality of fingers, wherein each of the plurality of fingers is configured to extend through a corresponding aperture of the septum seal. The return spring includes a collar portion and a plurality of spokes extending radially outward from the collar portion. At least a portion of the return spring may be sandwiched between the lower seal support and the upper seal support. The plurality of spokes is configured to bias the seal assembly toward a radial center of a housing.

17 Claims, 21 Drawing Sheets

Related U.S. Application Data continuation of application No. 14/430,359, filed as application No. PCT/US2013/061831 on Sep. 26, 2013, now Pat. No. 10,022,149.

(60) Provisional application No. 61/707,271, filed on Sep. 28, 2012, provisional application No. 61/707,293, filed on Sep. 28, 2012, provisional application No. 61/707,283, filed on Sep. 28, 2012.

(51) Int. Cl.
*A61B 17/02* (2006.01)
*A61B 17/00* (2006.01)

(52) U.S. Cl.
CPC ... *A61M 39/06* (2013.01); *A61B 2017/00862* (2013.01); *A61B 2017/346* (2013.01); *A61B 2017/3419* (2013.01); *A61B 2017/3452* (2013.01); *A61B 2017/3456* (2013.01); *A61M 2039/066* (2013.01); *A61M 2039/0626* (2013.01); *A61M 2039/0673* (2013.01); *A61M 2039/0686* (2013.01)

(58) Field of Classification Search
CPC .... A61B 2017/3419; A61B 2017/3452; A61B 2017/3456; A61M 39/06; A61M 2039/0626; A61M 2039/066; A61M 2039/0686
See application file for complete search history.

(56) References Cited

U.S. PATENT DOCUMENTS

| | | | |
|---|---|---|---|
| 5,271,380 A | 12/1993 | Riek et al. | |
| 5,290,245 A | 3/1994 | Dennis | |
| 5,308,336 A | 5/1994 | Hart et al. | |
| 5,314,417 A | 5/1994 | Stephens et al. | |
| 5,334,150 A | 8/1994 | Kaali | |
| 5,346,459 A | 9/1994 | Allen | |
| 5,366,478 A | 11/1994 | Brinkerhoff et al. | |
| 5,380,291 A | 1/1995 | Kaali | |
| 5,385,552 A | 1/1995 | Haber et al. | |
| 5,385,553 A | 1/1995 | Hart et al. | |
| 5,407,433 A | 4/1995 | Loomas | |
| 5,431,151 A | 7/1995 | Riek et al. | |
| 5,514,133 A | 5/1996 | Golub et al. | |
| 5,520,610 A | 5/1996 | Giglio et al. | |
| 5,524,501 A | 6/1996 | Patterson et al. | |
| 5,538,509 A | 7/1996 | Dunlap et al. | |
| 5,549,565 A | 8/1996 | Ryan et al. | |
| 5,551,947 A | 9/1996 | Kaali | |
| 5,569,205 A | 10/1996 | Hart et al. | |
| 5,569,291 A | 10/1996 | Privitera et al. | |
| 5,569,292 A | 10/1996 | Scwemberger et al. | |
| 5,591,192 A | 1/1997 | Privitera et al. | |
| 5,609,562 A | 3/1997 | Kaali | |
| 5,672,168 A | 9/1997 | de la Torre et al. | |
| 5,685,820 A | 11/1997 | Riek et al. | |
| 5,685,862 A | 11/1997 | Mahurkar | |
| 5,709,671 A | 1/1998 | Stephens et al. | |
| 5,720,730 A | 2/1998 | Blake, III | |
| 5,720,761 A | 2/1998 | Kaali | |
| 5,776,112 A | 7/1998 | Stephens et al. | |
| 5,792,113 A | 8/1998 | Kramer et al. | |
| 5,800,451 A | 9/1998 | Buess et al. | |
| 5,871,471 A | 2/1999 | Ryan et al. | |
| 5,893,875 A | 4/1999 | O'Connor et al. | |
| 6,007,481 A | 12/1999 | Riek et al. | |
| 6,093,176 A | 7/2000 | Dennis | |
| 6,099,505 A | 8/2000 | Ryan et al. | |
| 6,213,957 B1 | 4/2001 | Milliman et al. | |
| 6,355,028 B2 | 3/2002 | Castaneda et al. | |
| 6,478,806 B2 | 11/2002 | McFarlane | |
| 6,485,467 B1 | 11/2002 | Crook et al. | |
| 6,487,806 B2 | 12/2002 | Murello et al. | |
| 6,551,282 B1 | 4/2003 | Exline et al. | |
| 6,613,038 B2 | 9/2003 | Bonutti et al. | |
| 6,702,787 B2 | 3/2004 | Racenet et al. | |
| 6,736,797 B1 | 5/2004 | Larsen et al. | |
| 6,740,064 B1 | 5/2004 | Sorrentino et al. | |
| 6,811,546 B1 | 11/2004 | Callas et al. | |
| 6,830,578 B2 | 12/2004 | O'Heeron et al. | |
| 6,835,201 B2 | 12/2004 | O'Heeron et al. | |
| 6,855,128 B2 | 2/2005 | Swenson | |
| 6,884,253 B1 | 4/2005 | McFarlane | |
| 6,942,671 B1 | 9/2005 | Smith | |
| 6,960,164 B2 | 11/2005 | O'Heeron | |
| 7,276,075 B1 | 10/2007 | Callas et al. | |
| 7,320,694 B2 | 1/2008 | O'Heeron | |
| 7,370,694 B2 | 5/2008 | Shimizu et al. | |
| 7,393,322 B2 | 7/2008 | Wenchell | |
| 7,494,481 B2 | 2/2009 | Moberg et al. | |
| 7,678,046 B2 | 3/2010 | White et al. | |
| 7,686,823 B2 | 3/2010 | Pingleton et al. | |
| 7,708,713 B2 | 5/2010 | Albrecht et al. | |
| 7,744,569 B2 | 6/2010 | Smith | |
| 7,758,603 B2 | 7/2010 | Taylor et al. | |
| 7,794,644 B2 | 9/2010 | Taylor et al. | |
| 7,850,655 B2 | 12/2010 | Pasqualucci | |
| 7,918,827 B2 | 4/2011 | Smith | |
| 7,947,058 B2 | 5/2011 | Kahle et al. | |
| 7,985,232 B2 | 7/2011 | Potter et al. | |
| 3,002,750 A1 | 8/2011 | Smith | |
| 3,002,786 A1 | 8/2011 | Beckman et al. | |
| 3,012,128 A1 | 9/2011 | Franer et al. | |
| 8,029,475 B2 | 10/2011 | Franer et al. | |
| 8,052,653 B2 | 11/2011 | Gratwohl et al. | |
| 8,092,431 B2 | 1/2012 | Lunn et al. | |
| 8,109,873 B2 | 2/2012 | Albrecht et al. | |
| 8,118,735 B2 | 2/2012 | Voegele | |
| 8,128,590 B2 | 3/2012 | Albrecht et al. | |
| 8,137,318 B2 | 3/2012 | Schweitzer et al. | |
| 8,147,453 B2 | 4/2012 | Albrecht et al. | |
| 8,152,828 B2 | 4/2012 | Taylor et al. | |
| 8,206,411 B2 | 6/2012 | Thompson et al. | |
| 8,267,952 B2 | 9/2012 | Kahle et al. | |
| 8,398,666 B2 | 3/2013 | McFarlane | |
| 8,597,180 B2 | 12/2013 | Copeland et al. | |
| 8,961,406 B2 | 2/2015 | Ortiz et al. | |
| 10,022,149 B2 | 7/2018 | Holsten et al. | |
| 10,588,662 B2 * | 3/2020 | Holsten | A61B 17/3462 |
| 2002/0091410 A1 | 7/2002 | Ben-David et al. | |
| 2002/0173748 A1 | 11/2002 | McConnell et al. | |
| 2003/0109853 A1 | 6/2003 | Harding et al. | |
| 2004/0006356 A1 | 1/2004 | Smith | |
| 2004/0054353 A1 | 3/2004 | Taylor | |
| 2004/0073090 A1 | 4/2004 | Butler et al. | |
| 2004/0186434 A1 | 9/2004 | Harding et al. | |
| 2004/0204682 A1 * | 10/2004 | Smith | A61B 17/3462 604/167.06 |
| 2004/0215209 A1 | 10/2004 | Almond et al. | |
| 2004/0267204 A1 | 12/2004 | Brustowicz | |
| 2005/0010238 A1 | 1/2005 | Potter et al. | |
| 2005/0033342 A1 | 2/2005 | Hart et al. | |
| 2005/0070850 A1 | 3/2005 | Albrecht | |
| 2005/0070851 A1 | 3/2005 | Thompson et al. | |
| 2005/0070946 A1 | 3/2005 | Franer et al. | |
| 2005/0070947 A1 | 3/2005 | Franer et al. | |
| 2005/0192594 A1 | 9/2005 | Skakoon et al. | |
| 2005/0209608 A1 | 9/2005 | O'Heeron | |
| 2005/0212221 A1 | 9/2005 | Smith et al. | |
| 2005/0222582 A1 | 10/2005 | Wenchell | |
| 2005/0251190 A1 | 11/2005 | McFarlane | |
| 2006/0020281 A1 | 1/2006 | Smith | |
| 2006/0211992 A1 | 9/2006 | Prosek | |
| 2006/0217665 A1 | 9/2006 | Prosek | |
| 2006/0276751 A1 | 12/2006 | Haberland et al. | |
| 2007/0088277 A1 | 4/2007 | McGinley et al. | |
| 2007/0185453 A1 | 8/2007 | Michael et al. | |
| 2007/0239108 A1 | 10/2007 | Albrecht et al. | |
| 2007/0255218 A1 * | 11/2007 | Franer | A61B 17/3462 604/167.02 |
| 2008/0051739 A1 | 2/2008 | McFarlane | |

(56) References Cited

U.S. PATENT DOCUMENTS

| | | |
|---|---|---|
| 2008/0058723 A1 | 3/2008 | Lipchitz et al. |
| 2008/0146884 A1 | 6/2008 | Beckman et al. |
| 2008/0161758 A1 | 7/2008 | Insignares |
| 2008/0177265 A1 | 7/2008 | Lechot |
| 2008/0208222 A1 | 8/2008 | Beckman et al. |
| 2008/0249475 A1 | 10/2008 | Albrecht et al. |
| 2009/0093835 A1 | 4/2009 | Heinrich et al. |
| 2009/0234293 A1 | 9/2009 | Albrecht et al. |
| 2009/0275880 A1 | 11/2009 | Pasqualucci |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0222801 A1 | 9/2010 | Pingleton et al. |
| 2010/0228090 A1* | 9/2010 | Weisenburgh, II .......... A61B 17/3423 600/201 |
| 2010/0228096 A1 | 9/2010 | Weisenburgh, II et al. |
| 2010/0261975 A1 | 10/2010 | Huey et al. |
| 2010/0286706 A1 | 11/2010 | Judson |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118833 A1 | 5/2011 | Reichenbach et al. |
| 2011/0190592 A1 | 8/2011 | Kahle et al. |
| 2011/0201891 A1 | 8/2011 | Smith et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2012/0010569 A1 | 1/2012 | Parihar |
| 2012/0041371 A1 | 2/2012 | Tal et al. |
| 2012/0065590 A1 | 3/2012 | Bierman et al. |
| 2012/0109064 A1 | 5/2012 | Fischvogt et al. |
| 2012/0316596 A1 | 12/2012 | Taylor et al. |
| 2015/0065808 A1 | 3/2015 | Van Wyk et al. |
| 2015/0223833 A1 | 8/2015 | Coffeen et al. |
| 2018/0021063 A1 | 1/2018 | Main et al. |
| 2019/0059938 A1 | 2/2019 | Holsten |
| 2019/0059944 A1 | 2/2019 | Holsten |
| 2020/0246043 A1 | 8/2020 | Holsten et al. |

FOREIGN PATENT DOCUMENTS

| | | |
|---|---|---|
| EP | 1994896 A1 | 11/2008 |
| EP | 2145593 A1 | 1/2010 |
| JP | 2001525693 A | 12/2001 |
| JP | 2004532660 A | 10/2004 |
| JP | 2006187603 A | 7/2006 |
| JP | 2008289889 A | 12/2008 |
| JP | 2009534124 A | 9/2009 |
| JP | 2011515128 A | 5/2011 |
| WO | 9850093 A1 | 11/1998 |
| WO | 2006118650 A1 | 11/2006 |
| WO | 2012131746 A1 | 10/2012 |
| WO | 2014116889 A1 | 7/2014 |

OTHER PUBLICATIONS

European Search Report for counterpart EP Application No. EP13177088, dated Aug. 20, 2014, 7 pages.
Supplementary European Search Report EP13841230 dated May 19, 2016.
Japanese Office Action dated Mar. 21, 2017 in corresponding Japanese Application No. 2015-534640.
Australian Examination Report dated May 11, 2017 in corresponding Australian Application No. 2013323567.
Chinese Office Action dated Jul. 8, 2019 issued in corresponding CN Appln. 2017106972212.
Canadian Office Action dated Jul. 16, 2019 issued in corresponding CA Appln. 2,879,636.
Japanese Notice of Allowance dated Aug. 28, 2019 issued in corresponding JP Appln. No. 2018-212022.

* cited by examiner

OPTICAL TROCAR VISUALIZATION SYSTEM AND APPARATUS

CROSS-REFERENCE TO RELATED APPLICATIONS

This application is a continuation of U.S. patent application Ser. No. 16/034,745, filed Jul. 13, 2018, which is a continuation of U.S. patent application Ser. No. 14/430,359, filed Mar. 23, 2015, now U.S. Pat. No. 10,022,149, which is a National Stage Application of PCT/US2013/061831 under 35USC § 371 (a), filed Sep. 26, 2013, which claims benefit and priority of, U.S. Provisional Patent Application Ser. Nos. 61/707,271, 61/707,283, and 61/707,293, all entitled "OPTICAL TROCAR VISUALIZATION SYSTEM AND APPARATUS," and all filed on Sep. 28, 2012, the entire contents of each application being incorporated by reference herein.

BACKGROUND

Technical Field

The present disclosure relates to a visualization system and apparatus for tunneling through body tissue. More particularly, the present disclosure relates to an optical trocar which includes a transparent tunneling member which facilitates penetration of body tissue under direct observation.

Background of Related Art

Endoscopic and laparoscopic minimally invasive procedures have been used for introducing medical devices inside a patient and for viewing portions of the patient's anatomy. Typically, to view a desired anatomical site, a surgeon may insert a rigid or flexible endoscope inside the patient to render images of the anatomical site. In endoscopic surgical procedures, surgery is performed in any hollow organ or tissue of the body through a small incision or through narrow endoscopic tubes (cannulas) inserted through a small entrance wound in the skin. In laparoscopic procedures, surgical operations in the abdomen are performed through small incisions (usually about 0.5 to about 1.5 cm). Laparoscopic and endoscopic procedures often require the surgeon to act on organs, tissues and vessels far removed from the incision, thereby requiring that any instruments used in such procedures be of sufficient size and length to permit remote operation.

Typically, a trocar includes a cannula and a stylet or obturator. The cannula remains in place for use during the laparoscopic procedure, and the obturator includes a sharp tip for penetrating the body cavity. Most currently used trocars rely on protective tubes or relative retraction of the tip to prevent inadvertent contact with tissue.

Accordingly, the present disclosure is directed to further improvements in laparoscopic or visualization instruments.

SUMMARY

The present disclosure relates to a surgical system comprising a first obturator assembly and a second obturator assembly. The first obturator assembly includes a first obturator member and a first optical member. The first optical member is disposed adjacent a distal portion of the first obturator member. The first obturator member has a first diameter. A proximal portion of the first optical member has a second diameter. The second diameter is greater than or equal to the first diameter. The second obturator assembly includes a second obturator member and a second optical member. The second optical member is disposed adjacent a distal portion of the second obturator member. The second obturator member has a third diameter. The third diameter is equal to the first diameter. A proximal portion of the second optical member has a fourth diameter. The fourth diameter is different from the second diameter.

In disclosed embodiments, the surgical system further comprises a first cannula assembly. An inner diameter of an elongated portion of the first cannula assembly approximates the second diameter. Here, it is disclosed that the surgical system further comprises a second cannula assembly. An inner diameter of an elongated portion of the second cannula assembly approximates the fourth diameter. The inner diameter of the elongated portion of the second cannula assembly is different from the inner diameter of the elongated portion of the first cannula assembly.

In disclosed embodiments, the surgical system further comprises a third obturator assembly including a third obturator member and a third optical member disposed adjacent a distal portion of the third obturator member. The third obturator member has a fifth diameter, which is equal to the first diameter. A proximal portion of the third optical member has a sixth diameter, which is different from the second diameter and the fourth diameter.

In disclosed embodiments, the first diameter and the third diameter are each about 10 mm. Here, it is envisioned that second diameter is about 14 mm, and that the fourth diameter is about 10 mm.

In disclosed embodiments, a distal portion of the first obturator member includes a radially outward flared portion.

In disclosed embodiments, a distal portion of the first obturator member is encapsulated by the first optical member.

The present disclosure also relates to a method of manufacturing a plurality of obturator assemblies. The method comprises providing a tube including a first diameter, providing a first obturator member including a portion of the tube, providing a second obturator member including a portion of the tube, providing a first optical member having a second diameter, and providing a second optical member having a third diameter, which is different from the second diameter. The method also comprises engaging the first obturator member and the first optical member, and engaging the second obturator member and the second optical member.

In disclosed embodiments, engaging the first obturator member and the first optical member includes overmolding the first optical member onto the first obturator member.

In disclosed embodiments, the first diameter is about 10 mm. It is further disclosed that the second diameter is about 14 mm. It is further disclosed that the third diameter is about 10 mm.

In disclosed embodiments, the tube is made from at least one of steel and a polymeric material.

In disclosed embodiments, a distal portion of the first obturator member includes a radially outward flared portion.

In disclosed embodiments, a distal portion of the first obturator member is encapsulated by the first optical member.

In disclosed embodiments, the method further comprises providing a third obturator member including a portion of the tube, providing a third optical member having a fourth diameter, which is different from the second diameter and the third diameter, and engaging the third obturator member and the third optical member.

The present disclosure also relates to a surgical access device comprising an obturator assembly and a cannula assembly. The obturator assembly comprises an obturator member and a tip member disposed adjacent a distal portion of the obturator member. The obturator member has an outer diameter of about 10 mm. A portion of the tip member has an outer diameter of between about 14 mm and about 15 mm. The cannula assembly comprises an elongated portion configured to allow the obturator member and the tip member to slide therethrough. An inner diameter of the elongated portion approximates the outer diameter of the tip member.

The present disclosure also relates to a seal assembly for use with a surgical instrument. The seal assembly comprises a housing, a septum seal, a lower seal support, an upper seal support, and a return spring. The septum seal is disposed within the housing and includes an orifice and a plurality of apertures. The orifice is configured for providing a seal about a portion of an instrument inserted therethrough. The lower seal support includes an engagement surface. The engagement surface is configured to engage a portion of the septum seal. The engagement surface includes a plurality of apertures extending therethrough. The upper seal support includes a plurality of fingers, wherein each of the plurality of fingers is configured to extend through a corresponding aperture of the septum seal. The return spring includes a collar portion and a plurality of spokes extending radially outward from the collar portion. At least a portion of the return spring, e.g., a plurality of spaced apart radially inwardly extending protrusions, may be sandwiched between the lower seal support and the upper seal support. The plurality of spokes is configured to bias the seal assembly toward a radial center of a housing.

In disclosed embodiments, the septum seal includes a flat surface and an annular wall extending perpendicularly from a radial outer edge of the flat surface. Here, it is disclosed that the annular wall of the septum seal includes a lower portion in contact with the flat surface and an upper portion extending from the flat surface, and that the upper portion includes a peripheral seal in mechanical engagement therewith. Here, it is further disclosed that the peripheral seal extends radially outward from the upper portion of the annular wall.

In disclosed embodiments, the collar portion of the return spring is configured to be received at least partially within an annular channel of the lower seal support. It is also disclosed that the annular collar of the return spring is configured to engage the annular wall of the septum seal. Here, it is disclosed that the peripheral seal of the septum seal is configured to extend proximally of and in contact with a proximal edge of the annular collar of the return spring. Here, it is further disclosed that the entirety of the septum seal comprises an elastomeric material, and that the entirety of the septum seal comprises the same material. It is further disclosed that the return spring further includes a plurality of protrusions extending radially inward from the collar portion, and that each protrusion cooperates with corresponding fingers of the upper seal support for controlling rotational movement between the return spring and the septum seal.

The present disclosure also relates to a cannula assembly comprising a housing, an elongated portion extending distally from the housing and defining a longitudinal axis, and a seal assembly disposed at least partially within the housing. The seal assembly includes a septum seal, a lower seal support, an upper seal support, and a return spring. The septum seal includes an orifice and a plurality of apertures. The orifice is configured for providing a seal about a portion of an instrument inserted therethrough. The lower seal support includes an engagement surface. The engagement surface is configured to engage a portion of the septum seal. The engagement surface includes a plurality of apertures extending therethrough. The upper seal support includes a plurality of fingers, where each of the plurality of fingers is configured to extend through a corresponding aperture of the septum seal. The return spring includes a collar portion and a plurality of spokes extending radially outward from the collar portion. The return spring is configured to be received at least partially within a portion of the lower seal support. The plurality of spokes is configured to bias the seal assembly toward a radial center of the housing.

In disclosed embodiments, the septum seal includes a flat surface and an annular wall extending perpendicularly from a radial outer edge of the flat surface. Here, it is disclosed that the annular wall of the septum seal includes a lower portion in contact with the flat surface and an upper portion extending from the flat surface, and where the upper portion includes peripheral seal in mechanical engagement therewith. Here, it is further disclosed that the peripheral seal extends radially outward from the upper portion of the annular wall.

In disclosed embodiments, the collar portion of the return spring is configured to be received at least partially within an annular channel of the lower seal support. It is also disclosed that the annular collar of the return spring is configured to engage the annular wall of the septum seal. Here, it is disclosed that the peripheral seal of the septum seal is configured to extend proximally of and in contact with a proximal edge of the annular collar of the return spring. It is further disclosed that the return spring further includes a plurality of protrusions extending radially inward from the collar portion, and that each protrusion cooperates with corresponding fingers of the upper seal support for controlling rotational movement between the return spring and the septum seal.

In disclosed embodiments, at least a portion of at least one spoke contacts an interior wall of the housing.

In disclosed embodiments, the entirety of the septum seal is made from an elastomeric material.

The present disclosure relates to a cannula assembly comprising a housing and an elongated portion extending distally from the housing. The housing comprises a proximal housing component, a distal housing component, and a rotation prevention mechanism. The distal housing component is rotatably connectable to the proximal housing component. The rotation prevention mechanism is configured to prevent inadvertent relative rotation between the proximal housing component and the distal housing component. The rotation prevention mechanism is configured for selective actuation by a user, such that, when actuated, the proximal housing component is permitted to rotate with respect to and be disconnectable from the distal housing component.

In disclosed embodiments, the cannula assembly further comprises a seal disposed at least partially within the housing. Here, it is disclosed that the seal is accessible to a user when the proximal housing component and the distal housing component are disconnected from each other.

In disclosed embodiments, the rotation prevention mechanism includes a first component disposed on the proximal housing component, and a second component disposed on the distal housing component. Here, it is disclosed that the first component of the rotation prevention mechanism includes a finger that is integrally formed on a circumferential edge of the proximal housing component. Here, it is disclosed that the second component of the rotation prevention mechanism includes a tab. A user actuatable portion of the tab is pivotable with respect to the distal housing component between a first position and a second position. Here, it is further disclosed that a locking portion of the tab is moveable into and out of engagement with the finger upon pivoting the user actuatable portion of the tab between its first position and its second position, and where engagement between the locking portion of the tab and the finger prevents one or two directions of rotation between the proximal housing component and the distal housing component.

In disclosed embodiments, at least a portion of the tab is distally pivotable with respect to the distal housing component.

In disclosed embodiments, after engagement between the proximal housing component and the distal housing component, a predetermined amount of rotation of the proximal housing component with respect to the distal component causes the proximal housing component to be locked in one direction of rotation with respect to the distal housing component.

In disclosed embodiments, after engagement between the proximal housing component and the distal housing component, a predetermined amount of rotation of the proximal housing component with respect to the distal component causes the proximal housing component to be locked in both directions of rotation with respect to the distal housing component.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
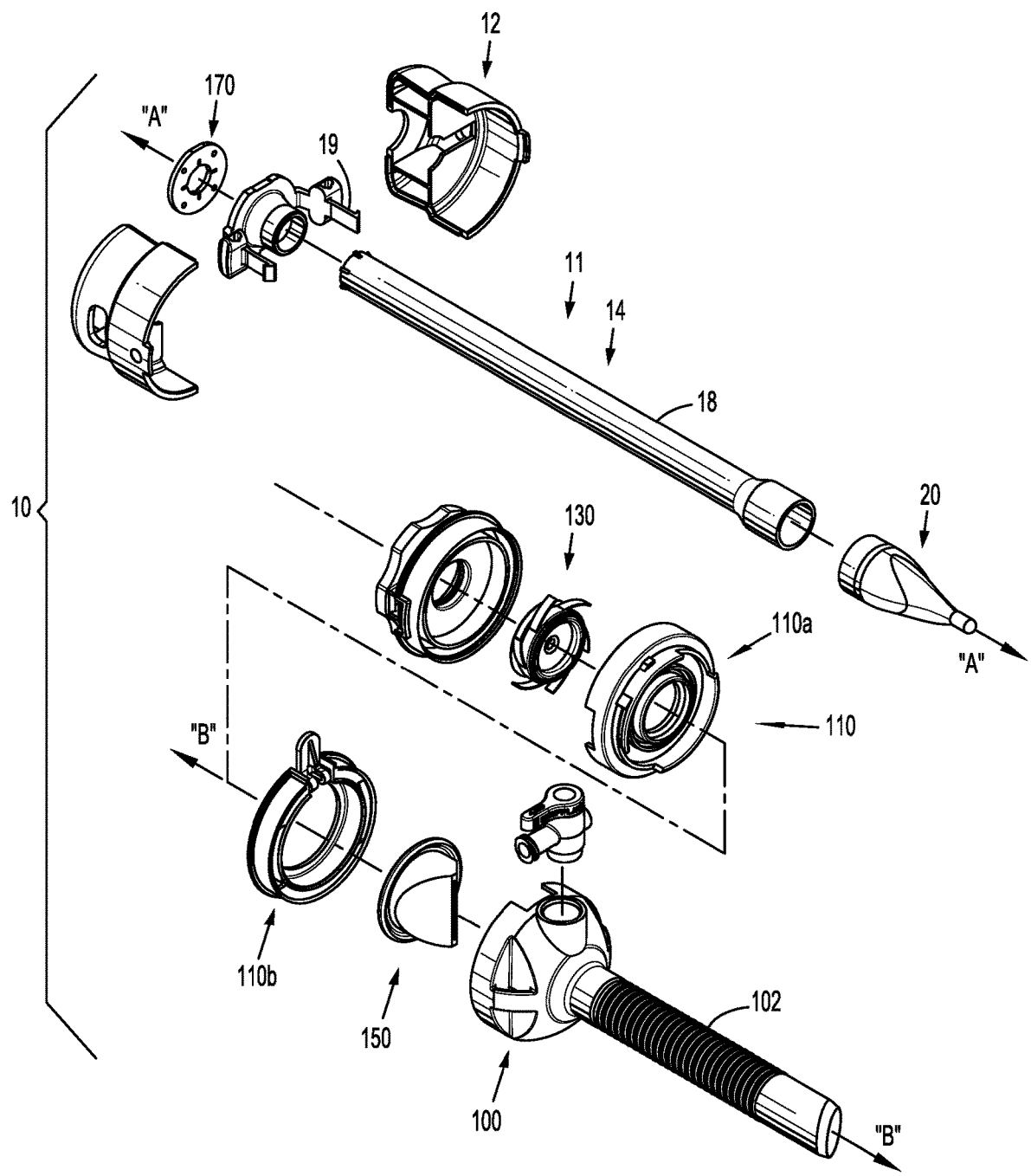
FIG. 1 is a perspective view with parts separated of a surgical visualization system in accordance with embodiments of the present disclosure illustrating the optical access apparatus and a cannula assembly.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Various embodiments of the surgical visualization device and system disclosed herein may be employed in endoscopic, laparoscopic, open surgical procedures, interventional and/or intralumenal procedures such as GI sheathing (metabolic/bariatric) and/or banding, and/or for more advanced minimally invasive procedures such as those which employ a device that facilitates multiple instrument access through a single opening and permits a user to operate through a single entry point, i.e., navel, vagina and/or anus, where additional visualization due to compromising space, is required. In addition, the system of the present disclosure may be utilized for post-operative monitoring, diagnostics and combinations thereof.

In embodiments, the visualization apparatus and system of the present disclosure may be utilized in lieu of or in addition to a traditional scope and/or surgical instrument, and the apparatus may be specifically designed for use with instruments including an endoscope and additional instruments such as graspers, staplers, forceps or the like introduced within a portal member to carry out the surgical procedure, and/or other access devices. An example of such a surgical portal is disclosed in U.S. Patent Application Publication No. 2009/0093752 A1, filed Oct. 2, 2008, the entire contents of which are hereby incorporated by reference. Additionally, the entire contents of U.S. Provisional Patent Application Ser. No. 61/548,428 filed on Oct. 18, 2011 are hereby incorporated by reference herein.

In embodiments, the device may be used to guide other instruments by sight or electronically to very precise anatomical sites, such as for example tumor and/or disease sites. In embodiments, for example, the apparatus may be utilized for complex thoracic surgeries where the apparatus may be positioned at the chest wall or lung directly for added visualization of critical vessels and/or pulmonary structures.

Various embodiments of the visualization apparatus of the present disclosure may comprise devices inserted in a patient to provide visualization of the target site. These devices may be introduced into the patient using minimally invasive procedures through natural orifices such as those mentioned above, or via a device inserted through a trocar, for example, and may be adapted to provide images of the surgical site or anatomic location such as the lungs, liver, stomach, gall bladder, urinary tract, reproductive tract, and intestinal tissue, for example. Once positioned at the target site, the surgical visualization devices provide images that enable the surgeon to more accurately diagnose and provide more effective treatment of the diseased tissue. In embodiments, the visualization apparatus may be inserted into the tissue treatment region percutaneously. In other embodiments, the surgical visualization device may be introduced into the tissue treatment region endoscopically (e.g., laparoscopically and/or thoracoscopically), through small keyhole incisions via a trocar, or through a natural orifice.

Embodiments of the surgical visualization devices may provide images of the desired tissue during in-vivo treatment procedures used to ablate or destroy live cancerous tissue, tumors, masses, lesions, and other abnormal tissue growths present at the tissue treatment site.

In embodiments, a bladeless optical access system may be provided that permits separation of tissue planes in a surgical procedure and visualization of body tissue fibers as they are being separated, thereby permitting a controlled traversal across a body wall. In embodiments, a bladeless trocar may be provided that enables insufflation of a body cavity and contemporaneous visualization thereof through the distal tip of an obturator. In embodiments, the bladeless trocar or obturator may be provided for the blunt dissection of the abdominal lining during a surgical procedure.

Figure 2:
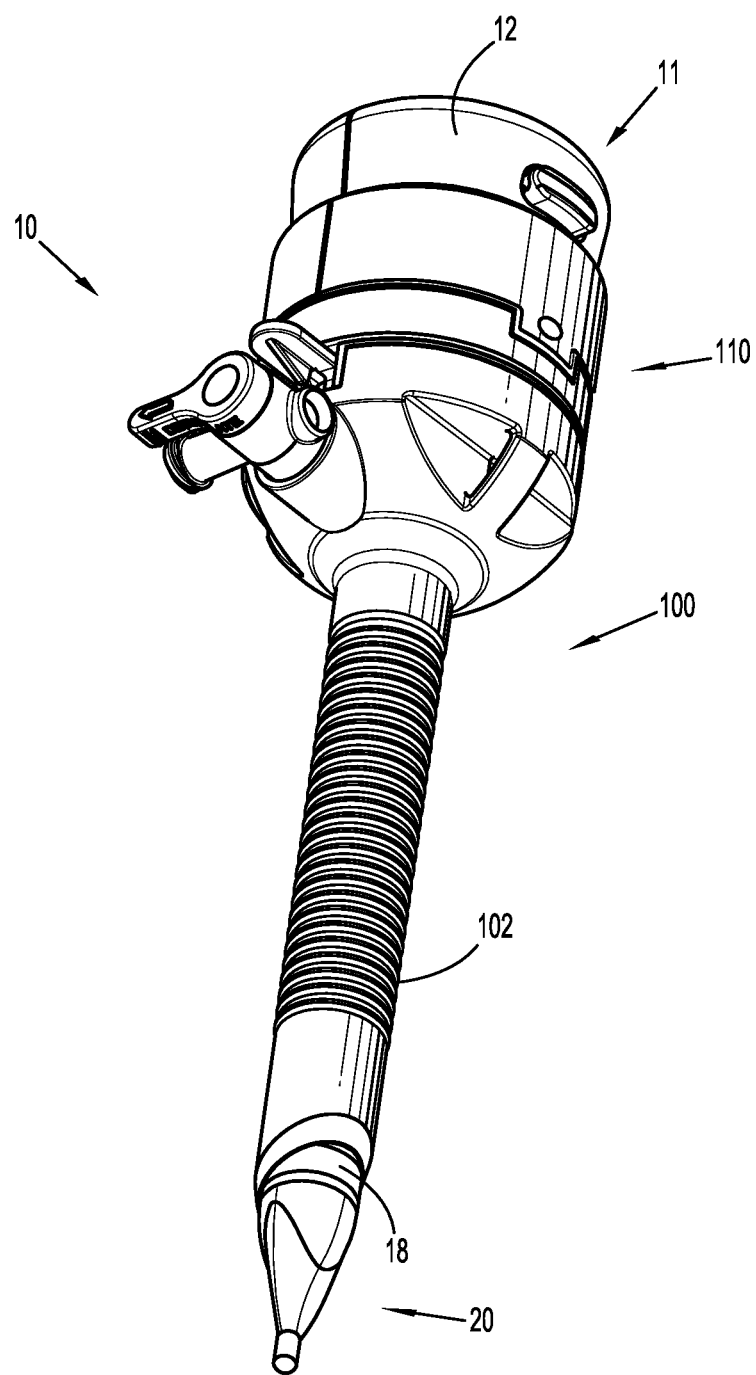
FIG. 2 is a perspective view of the surgical visualization system in accordance with the embodiment of FIG. 1.

Referring now to FIGS. 1 and 2, there is illustrated a surgical visualization system 10 in accordance with the present disclosure. In embodiments, system 10 may include an obturator assembly or optical access apparatus 11 and a cannula assembly 100 which is configured to at least partially receive the obturator assembly 11. The obturator assembly 11 includes an obturator housing 12 disposed in mechanical cooperation with an elongated obturator member or trocar 14, which defines a longitudinal axis "A-A." The obturator member 14 extends distally from the obturator housing 12. The terms "obturator assembly" and "optical access apparatus," and the terms "obturator member," "trocar" and "elongated obturator tubular member" are used interchangeably herein and are intended to include any or all of the mechanisms known in the art for separating tissue planes in a surgical procedure and for the blunt dissection of cavity linings and/or organs during a surgical procedure.

The obturator member 14 includes an obturator shaft 18 mechanically engagable with the obturator housing 12. The obturator member 14 also includes an optical member or tunneling member 20 at the distal end of the obturator shaft 18.

The cannula assembly 100 of the surgical visualization system 10 includes a clear (i.e., transparent or translucent) elongated portion 102, defining a longitudinal axis "B-B," and a cover 110. The cover 110 encloses an insert seal assembly 130 and a zero-closure seal 150. The insert seal assembly 130, which is configured to provide a seal about a surgical instrument inserted therethrough, is disposed proximally of the zero-closure seal 150, which is configured to prevent gasses from proximally exiting cannula assembly 100 when in the absence of a surgical instrument inserted therethrough. More particularly, cover 110 includes a proximal section 110a and a distal section 110b, which are selectively engageable with each other, as discussed below.

In embodiments, a distal end of the optical access apparatus 11 may include a tunneling or optical member 20, at least a portion of which being translucent or transparent. The terms "tunneling member," "optical member" and "overmolded attachment" are used interchangeably herein and are intended to include any or all of the mechanisms known in the art for blunt tip members utilized for attachment to obturator, trocar and cannula assemblies for separating tissue planes in a surgical procedure and for the blunt dissection of cavity linings and/or organs during a surgical procedure.

Figure 4:
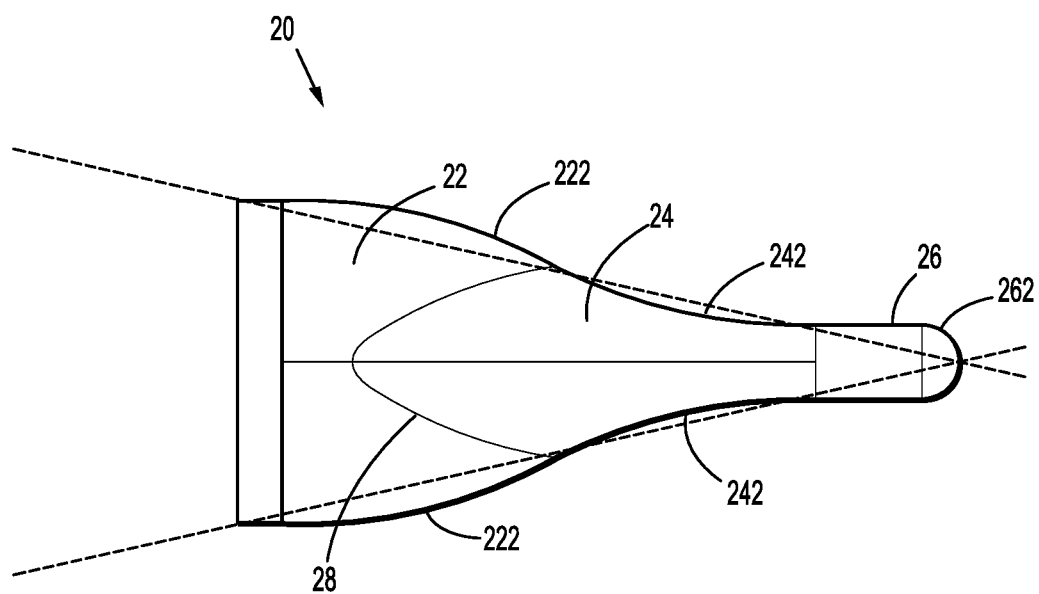
FIG. 4 is a top view of the optical member end of FIG. 1.
Figure 5:
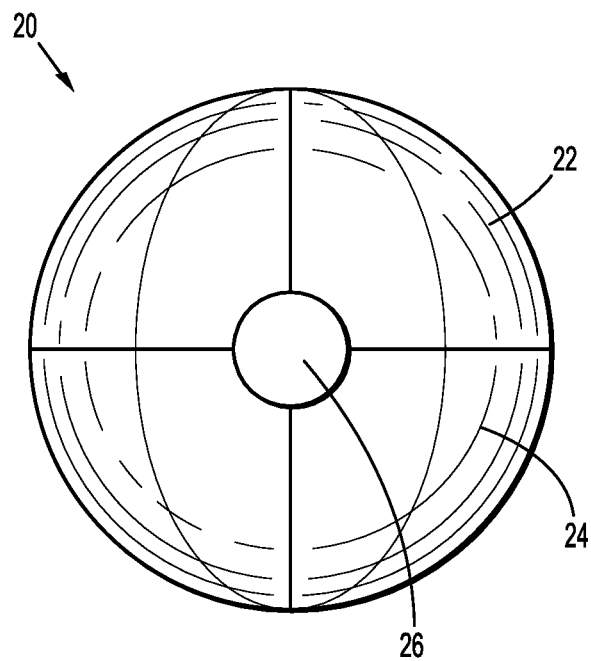
FIG. 5 is an axial view of the optical member of FIG. 3.
Figure 6:
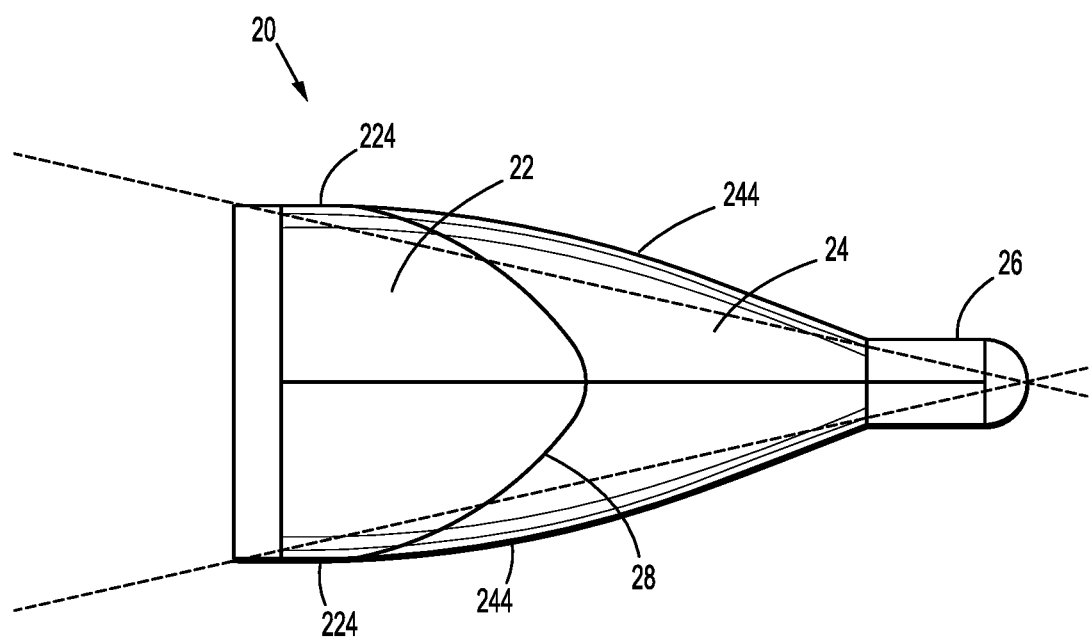
FIG. 6 is a side view of the optical member end radially offset 90° relative to the top view of FIG. 4.
Figure 6A:
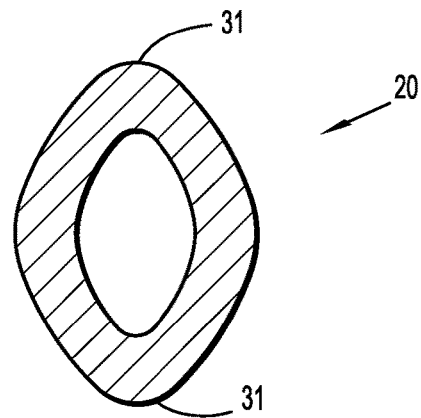
FIG. 6A is a cross sectional view of the optical member of FIG. 6 taken at approximately the longitudinal midpoint thereof.
Figure 6B:
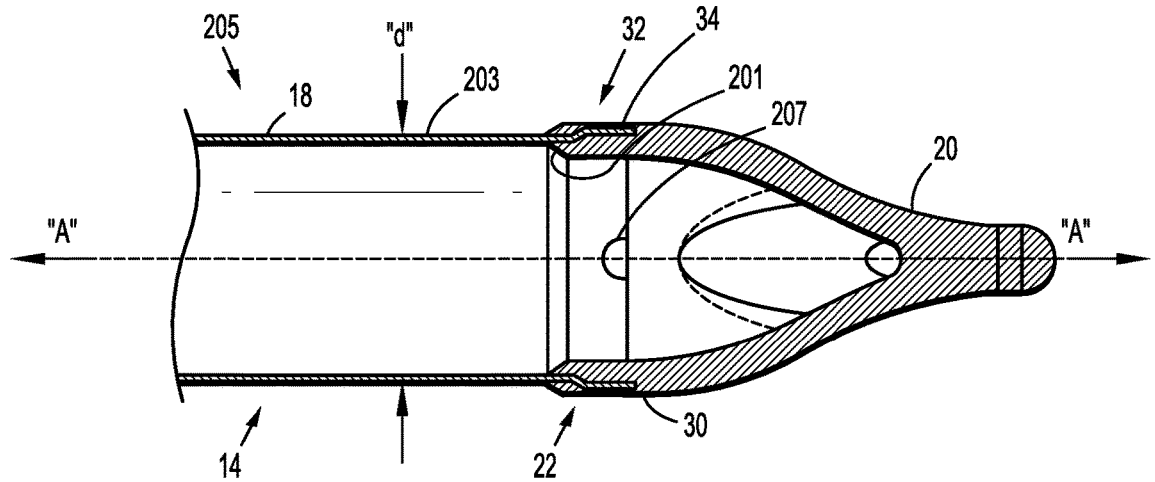
FIG. 6B is a cross sectional view of the elongated tubular member distal end region and optical member of the optical access apparatus of FIG. 1.
Figure 6C:
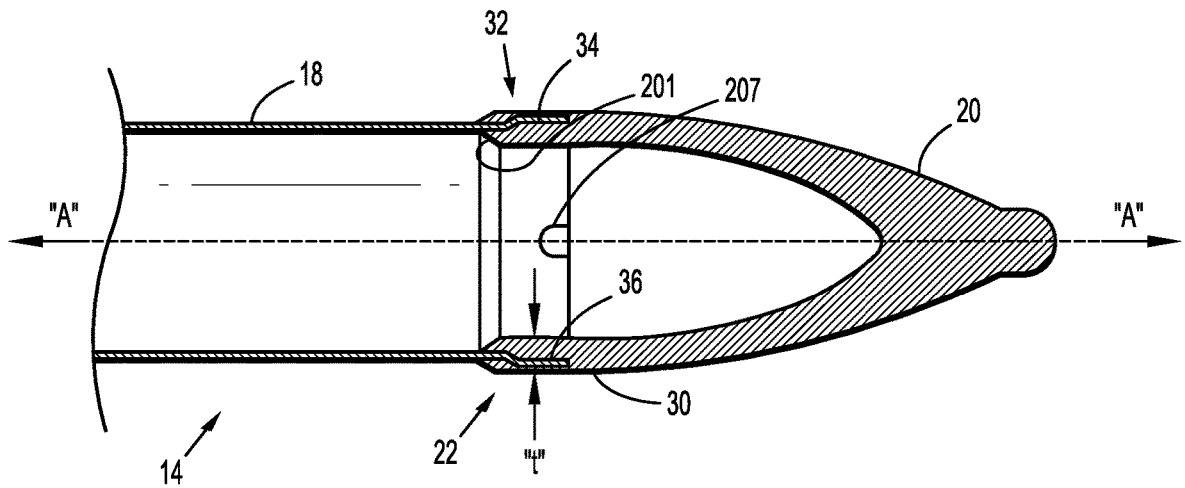
FIG. 6C is a cross sectional view of the elongated tubular member distal end region and optical member of the optical access apparatus of FIG. 6B with an endoscope positioned therein.

With particular reference to FIGS. 3-6C, optical member 20 may be substantially hollow to receive the distal end of an endoscope (FIG. 6C). A distal viewing tip of an endoscope may be brought into engagement with a sloped surface 201 within the optical member 20, as will be described hereinbelow. Improved optical characteristics of the system permit precise and accurate visual placement thereof into a body cavity. Accordingly, the access system may be suitable as an initial entry surgical access system.

Figure 3:
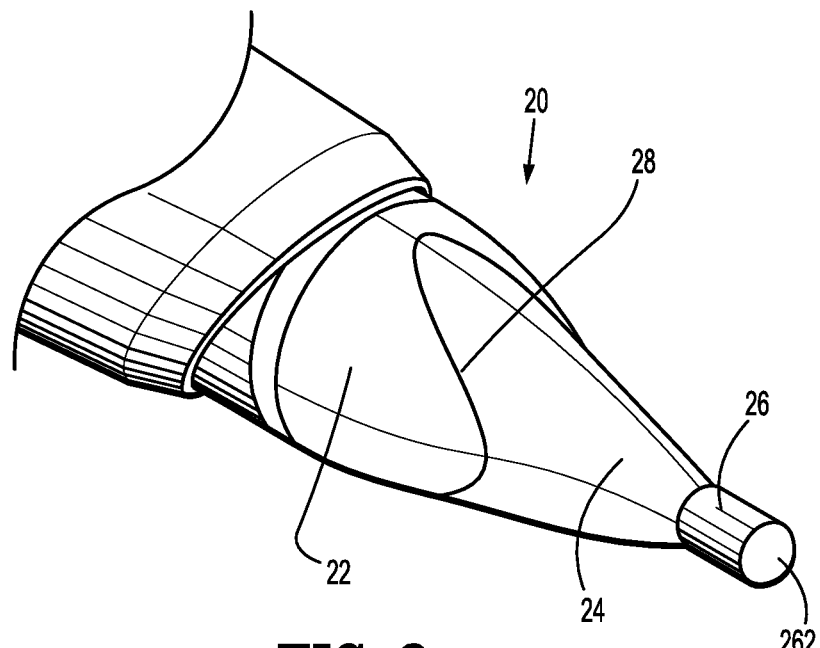
FIG. 3 is an enlarged perspective view of the tunneling or optical member end of the access member of the optical access apparatus in accordance with the embodiment of FIGS. 1-2.

With reference to FIGS. 3 and 4, the optical member 20 includes a proximal section 22, a central section 24, and an atraumatic guiding nub 26. An imaginary line 28 (shown to illustrate curvature) delineates the boundary between the proximal section 22 and the central section 24.

In embodiments, the tunneling or optical member 20 is a bladeless tip configured for traversing and/or penetrating body tissue. In other embodiments, the tunneling member 20 may be configured with for example, a sharp tip, a pointed tip, a pyramidal tip, a bladed tip, a conical tip, and/or a tip comprising one or more sharp edges or sharpened edges. In still other embodiments, the tunneling member 20 may be a radiused blunt tip, which may be helpful for traversing an existing body orifice, and/or relatively soft or fatty tissue.

FIG. 4 illustrates a top view of the optical member 20. As depicted, the proximal section 22 includes a pair of diametrically opposed convex surfaces 222, and the central section 24 includes a pair of diametrically opposed concave surfaces 242. The atraumatic guiding nub 26 extending distally from the central section 24, is generally cylindrical, and includes a rounded end 262. The rounded end 262 defines a radius of curvature dimensioned to be atraumatic to tissue. Additionally, as shown in connection with phantom lines that represent a cone, a portion of both the proximal section 22 and the atraumatic guiding nub 26 of optical member 20 are outside of the dimensions of the cone.

In embodiments, tunneling member 20 may include the atraumatic guiding nub 26 characterized by having a nipple configuration nose with a rounded tip. In embodiments, the atraumatic guiding nub or nose 26 may be generally tapered defining a simple curved arrangement.

With reference to FIG. 5, an end or axial view of the optical member 20 illustrates the circular profile of the guiding nub 26, the oval profile of the central section 24, and the circular profile of the proximal section 22.

FIG. 6 shows a side view of the optical member 20 radially offset 90° relative to the top view of FIG. 4. As shown, the proximal section 22 of the optical member 20 further includes a pair of diametrically opposed outer surfaces 224 which are generally linear and/or convex. The central section 24 also includes a pair of opposed outer surfaces 244 which are convex. Thus, in embodiments, the central section 24 of the optical member 20 is inclusive of both concave surfaces 242 (FIG. 4) and convex surfaces 244 (FIG. 6) however, it is envisioned that the optical member 20 may include only one type of surface, either concave or convex (not shown). Alternatively, in embodiments, it is envisioned that rounded tip 226 may be more pointed than the embodiment illustrated.

Additionally, as shown in connection with the phantom lines in FIG. 6 that represent a cone, a portion of the proximal section 22, the central section 24, and the atraumatic guiding nub or tip 26 of optical member 20 are outside of the dimensions of the cone.

The atraumatic guiding nub 26 permits initial insertion within an opening, e.g., a pre-cut scalpel incision, in the tissue and facilitates the advancement of the optical member 20 between the tissue layers to gently dissect tissue, e.g., without any cutting or incising of the tissue. After initial insertion and continued distal insertion, the central section 24 and the proximal portion 22 continue to gently enlarge the opening in tissue.

FIG. 6A is a cross-sectional view of the optical member 20 taken at approximately the longitudinal midpoint thereof. The figure illustrates that the optical member 20 includes rounded outer surfaces 31 that function to help separate tissue along the tissue planes and minimize the potential of undesired or unintended piercing of tissue.

With reference to FIGS. 6B and 6C, the optical member 20 may be fabricated from a polymeric material and is transparent or translucent to permit passage of light rays. During assembly, the optical member 20 is overmolded onto the obturator shaft 18 to connect the components. In particular, the obturator shaft 18 includes a distal shaft section which depends radially inwardly relative to the longitudinal axis A-A and includes at least one slot 207. The optical member 20 is molded to encapsulate the distal shaft section and is secured to the obturator shaft 18 by engaging the at least one slot upon curing of the polymeric material.

In embodiments, the optical member 20 defines an internal chamfered or sloped surface 201 which is obliquely arranged relative to the longitudinal axis A-A. The chamfered surface 201 is able to be directly engaged by the outermost periphery of the distal end of the endoscope (see FIG. 6C) such that light transmitted from regions of the endoscope radially within the outer periphery travel across an air gap prior to being received by the chamfered or sloped surface 201. The optical member 20 permits the passage of light rays to enable viewing (with the endoscope) tissue adjacent the optical member 20 during the insertion and/or advancement of the surgical visualization system 10.

In embodiments, elongated tubular member 14 includes a first diameter "d" at a location 203 within a distal region 205.

Additionally, as discussed above, trocar 14 is configured for insertion through cannula assembly 100. Further, cannula assemblies 100 typically vary in diameter (e.g., inner diameters of 11 mm, 12 mm, or 15 mm) depending on the surgical task to be performed, area of operation, preference of surgeon, etc. Typically, once a cannula assembly 100 having a particular diameter is selected, the obturator member 18 (of a trocar 14) having a corresponding diameter (i.e., the outer diameter of the obturator member 18 is slightly smaller than the inner diameter of the cannula assembly 100) is likewise chosen. That is, obturator members 18 are typically manufactured with different diameters—one size obturator member 18 for each size cannula assembly 100.

In embodiments of the present disclosure, a single obturator member 18 (having one diameter "d" (notwithstanding the change in diameter at a distal portion 32 thereof, as discussed below) is configured for use with cannula assemblies 100 having different diameters. Here, the optical member 20 is configured such that an outer surface 30 of its proximal portion 22 is dimensioned to provide a desired fit within the elongated portion 102 of cannula assembly 100. It is contemplated that a desired fit between trocar 14 and cannula 100 results in optical member 20 having little or no radial movement or "play" when inserted through cannula 100. More particularly, with reference to FIGS. 6B and 6C, distal portion 32 of obturator member 18 includes a radially outward flared portion 34, and optical member 20 is overmolded such that optical member 20 at least partially encapsulates flared portion 34. Further, the thickness "t" of a wall 36 of optical member 20 is dimensioned to help ensure outer surface 30 of proximal portion 22 provides the desired fit between obturator member 11 and the elongated portion 102 of the cannula assembly 100.

For example, when a 15 mm cannula is used, the obturator member 18 has an outer diameter slightly greater than 10 mm, and the widest portion (e.g., proximal portion 22) of the optical member 20 has an outer diameter slightly less than the inner diameter of the 15 mm cannula; when a 12 mm cannula is used, obturator member 18 has an outer diameter slightly greater than 10 mm, and the widest portion of the optical member 20 has an outer diameter slightly less than the inner diameter of the 12 mm cannula; and when an 11 mm cannula is used, the obturator member 18 has an outer diameter slightly greater than 10 mm, and the widest portion of the optical member 20 has an outer diameter slightly less than the inner diameter of the 11 mm cannula. Thus, as can be appreciated, a single diameter tube (e.g., a 10 mm steel or polymeric tube) may be used for manufacturing several obturator assemblies 11 for use with a variety of sizes (e.g., 11 mm, 12 mm and 15 mm) of cannula assemblies 100. As a result, manufacturing costs may be significantly reduced.

The present disclosure also relates to a method of manufacturing surgical visualization systems 10, or components thereof.

As mentioned above, elongated tubular member 14 of the optical access apparatus 11 may be dimensioned and configured to receive therein any suitable endoscope (FIG. 6C) and/or laparoscope (not shown), which typically includes an imaging element and fiber optic light fibers (not illustrated).

The endoscope may be positioned within optical access apparatus 11 and the assembled unit is advanced through an incision and into the body cavity. During the advancement within tissue, the endoscope permits constant visualization of the neighboring tissue thereby providing confirmation upon entering into the body cavity while also minimizing undesired contact or engagement with any underlying organs or other body tissues. Alternatively, in embodiments, the endoscope may be positioned within optical access apparatus 11 after the optical access apparatus 11 has been advanced into the body cavity.

The endoscope may be any conventional scope suitable for endoscopic applications including, e.g., a laparoscope, arthroscope, colonoscope, etc. The endoscope may incorporate an optical train or lens arrangement which is capable of transmitting an image of an object from the distal or objective lens through the eyepiece or monitor for viewing by the surgeon. Thus, although the endoscope may include an eyepiece at its proximal end, the endoscope additionally or alternatively may be connected to a monitor.

In embodiments, at least a portion of the wall of the tunneling member 20 includes a thin-wall configuration. The thin-wall configuration enables light to travel through the material with reduced loss in intensity, thereby enhancing the visibility of tissue through the tunneling member 20 as the optical access apparatus 11 is advanced and placed into the targeted body cavity. The thin-wall configuration also reduces distortion of the image viewed through the tunneling member 20 and maintains the color accuracy of the viewed tissue. In embodiments, the wall thicknesses of tunneling member 20 may be from about 0.02 inches (about 0.5 mm) to about 0.025 inches (about 0.65 mm). In other embodiments, the tip wall may be thicker, for example, to provide additional strength.

All transparent or translucent materials may have a light transmittance value of less than about 100%. That is, less than about 100% of the light incident on the material is transmitted directly through the material. For a given transparent or translucent material, as the wall thickness of the material increases, the amount of light that travels through the material decreases. In embodiments, a reduced wall thickness may reduce the loss of light or absorption thereby improving the image of the tissue through which the elongated tubular member 14 is advanced, and maintaining the color accuracy and fidelity of the observed tissue.

The device may include a pair of vent holes (not shown) at the rounded end 262 of the optical access apparatus 11, through which an insufflating gas, such as carbon dioxide, flows into a body cavity, as discussed in greater detail below.

The optical access apparatus 11 may be manufactured from any material known to those skilled in the art by any known molding techniques which is suitable for accessing body tissue. In embodiments, each of the components of the optical access apparatus 11 may include different materials. In embodiments, suitable materials may also include, for example, biocompatible metals such as stainless steel, titanium and the like, ceramics, silicones and the like. Some embodiments of the optical access apparatus 11 may further include a composite, for example, a fiber-reinforced polymer. In some embodiments, a stronger material permits reducing a wall thickness of a component without reducing the strength thereof. For example, some embodiments of a metal or composite elongated tubular member 14 are thinner than a corresponding polymer version, thereby increasing the diameter of a lumen thereof without increasing the outer diameter. In embodiments, elongated tubular member or obturator 14 may be transparent or translucent throughout its entire length. Alternatively, only tunneling member 20 of elongated tubular member 14 may be transparent or translucent.

In embodiments, the elongated tubular member 14 may include a biocompatible metal material, for example, a stainless steel tube, and the tunneling member 20 may be a thermoplastic elastomeric, such as for example, LEXAN®, commercially available from SABIC Innovative Plastics Holding BV, insert molded onto the elongated tubular member. In embodiments, the metal tube may have a wall thickness as thin as about 0.003 inches (about 0.076 mm).

In embodiments, the cannula 100 may include a rigid material. In embodiments, the obturator may include a rigid material and/or a flexible material because the obturator may be largely supported by the cannula during use.

The method of forming or overmolding the tunneling member 20 to the distal region 205 of the elongated tubular member 14 will now be discussed. In embodiments, any suitable material for forming the tunneling member 20 as described above may be utilized. In embodiments, an elastomeric material may be configured to flow into the at least one slot or piercing 207 of the elongated tubular member 14.

Figure 7:
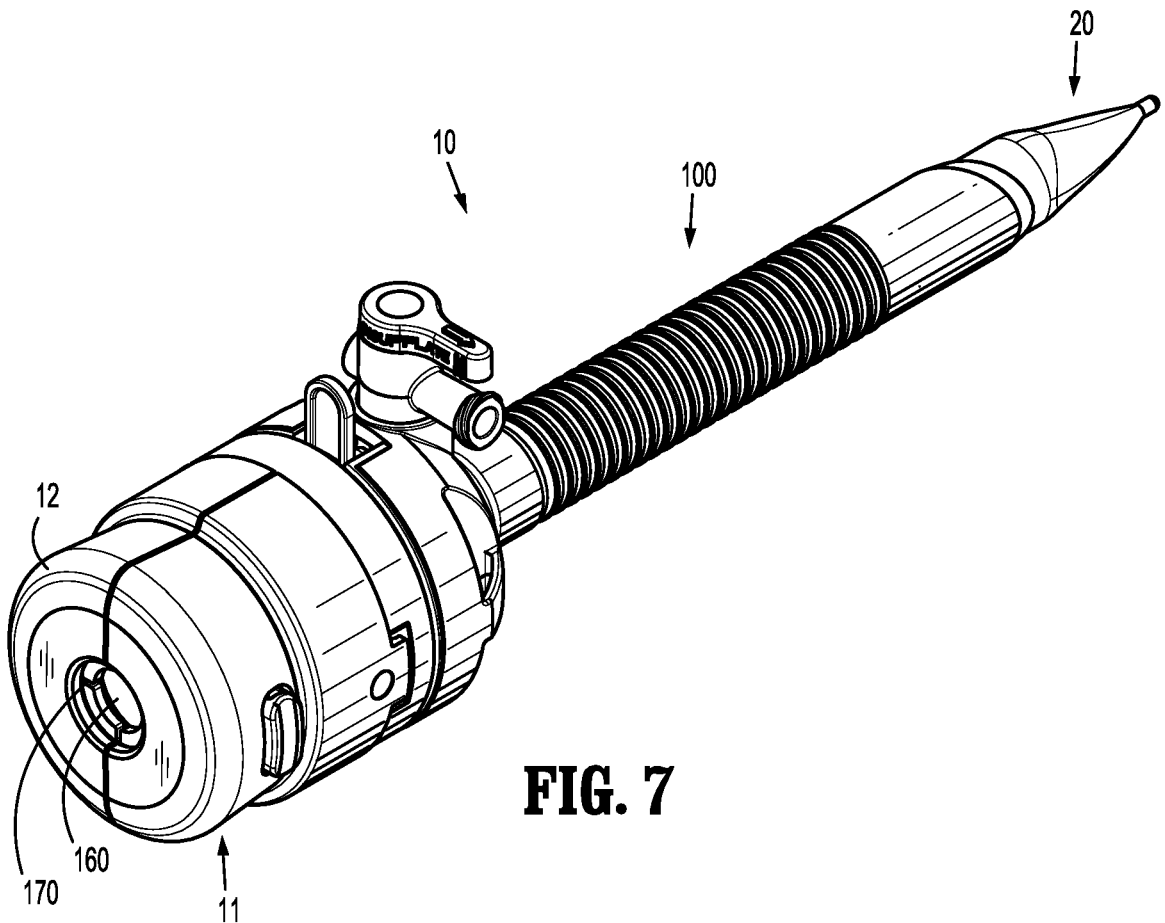
FIG. 7 is a perspective view of a cover and the cannula assembly of FIG. 1.
Figure 8:
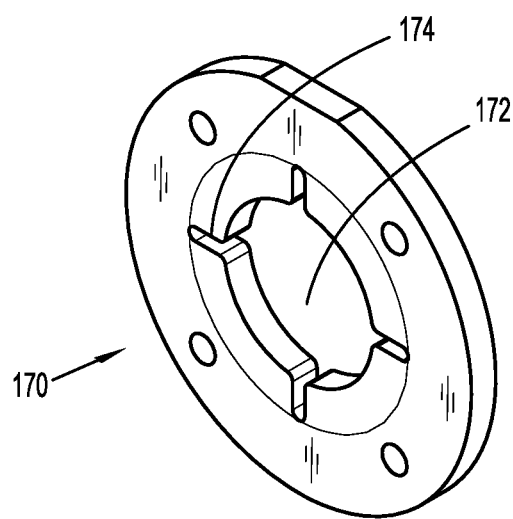
FIG. 8 is a perspective view of the cover of the cannula assembly of FIG. 1.
Figure 9:
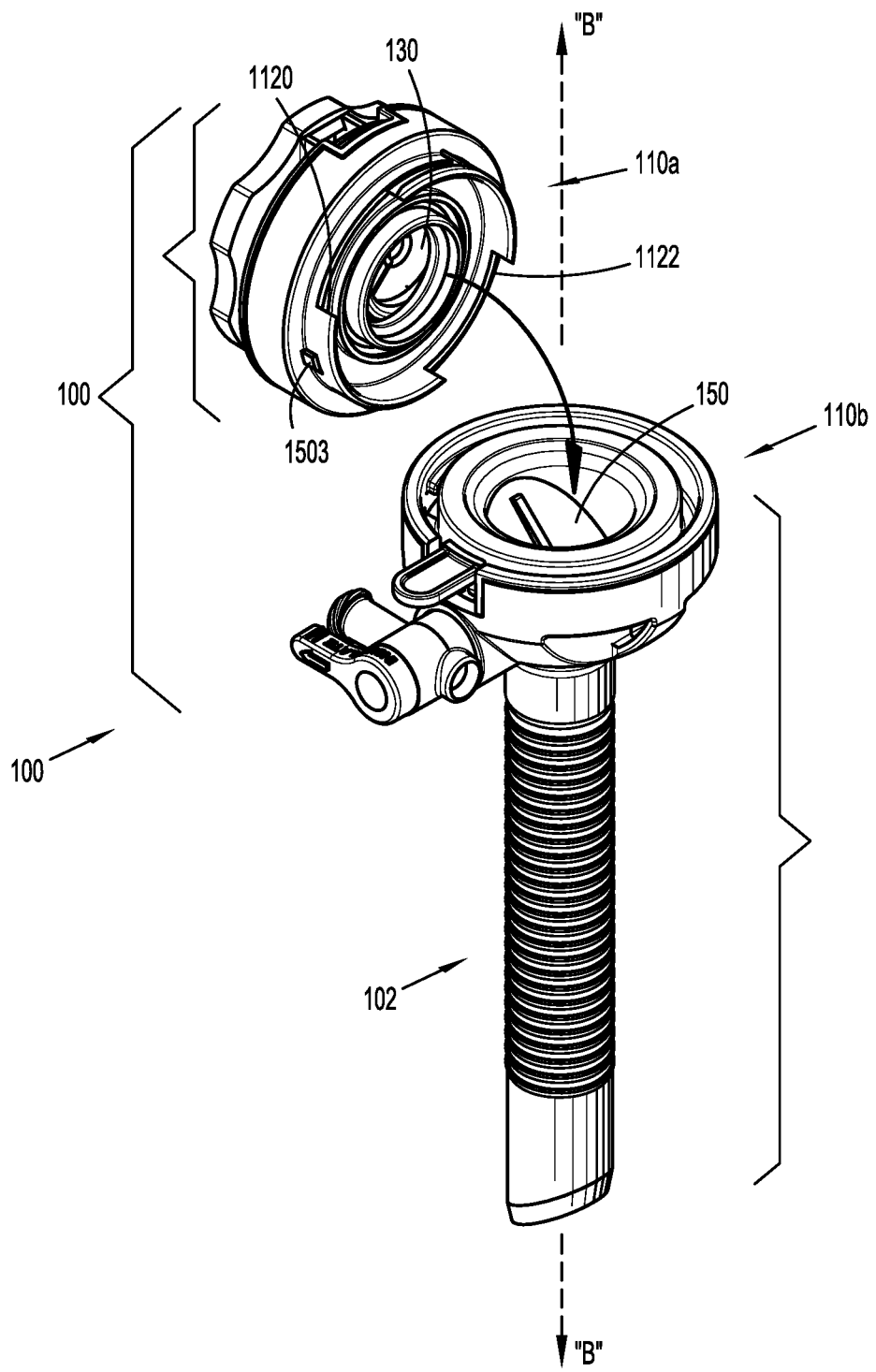
FIG. 9 is a perspective view of the cannula assembly showing a proximal housing component separated from a distal housing component.
Figure 11:
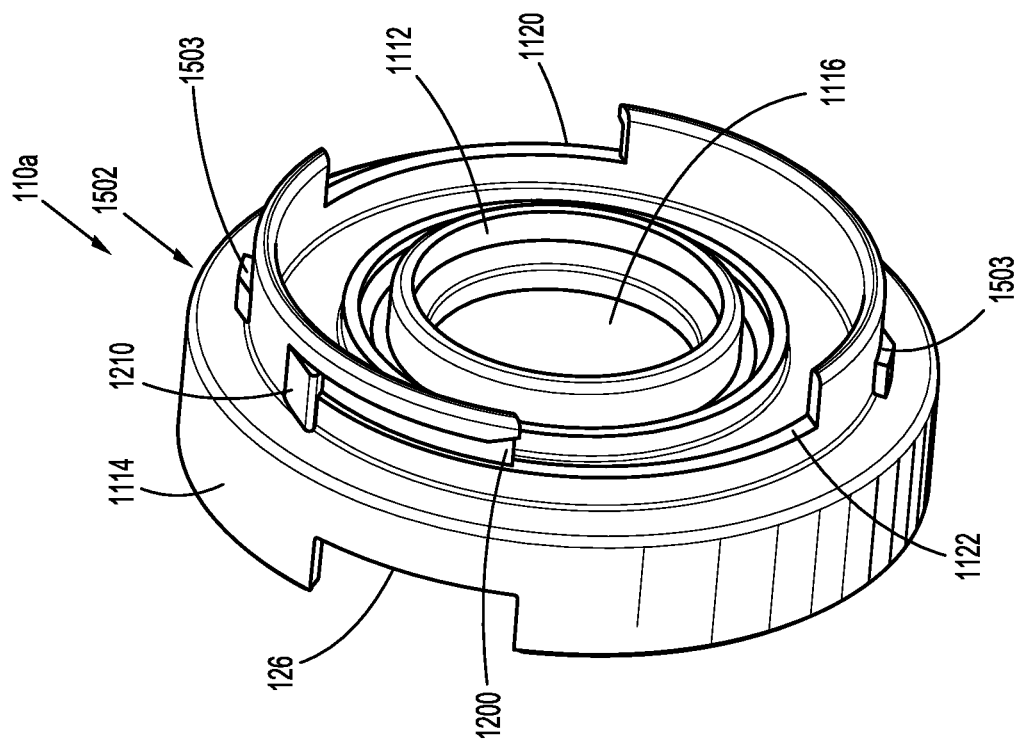
FIG. 11 is a perspective view of the proximal housing component.
Figure 10:
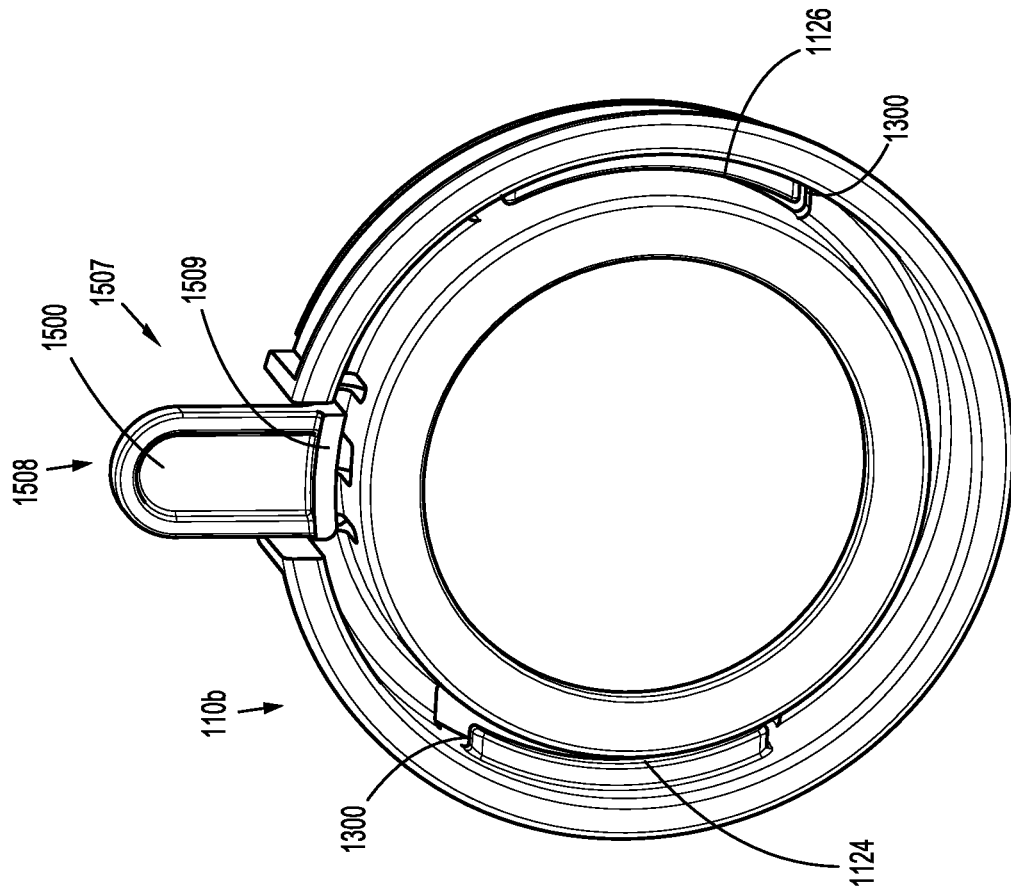
FIG. 10 is a perspective view of the distal housing component viewed from the proximal side.

The obturator housing 12 will now be discussed in more detail with reference to FIGS. 7 and 8. The obturator housing 12 of the obturator assembly 11 includes an opening 160 (FIG. 7) and a scope retention member 170 (FIG. 8) adjacent the opening 160. It is envisioned that scope retention member 170 is fabricated from an elastomeric material. Scope retention member 170 defines a central opening 172 for receiving the endoscope and includes four radial slits 174 extending outwardly from the central opening 172. The radial slits 174 permit flexure of the scope retention member 170 and enlargement of the central opening 172 upon insertion of the endoscope. The scope retention member 170 is adapted to engage the outer surface of the endoscope in frictional engagement therewith to assist in retaining the relative positioning of the endoscope within the obturator assembly 11.

The cannula assembly 100 will now be discussed in detail with reference to FIGS. 9-14. As mentioned above, the cannula assembly 100 includes an elongated portion 102, defining a longitudinal axis "B-B," and a cover 110. The cover 110, which includes a proximal housing component 110*a* and a distal housing component 110*b*, encloses insert seal assembly 130 and a zero-closure seal 150. The insert seal assembly 130 is disposed proximally of the zero-closure seal 150. More particularly, proximal housing component 110*a* encloses insert seal assembly 130, and distal housing component 110*b* encloses zero-closure seal 150.

The cover 110 is configured to mechanically engage a proximal portion of the elongated portion 102 and helps maintain the insert seal assembly 130 and the zero-closure seal 150 therein. Cover 110 also includes a pair of notches 126 (FIG. 11) thereon. Notches 126 are configured to be mechanically engaged by a pair of latches 19 disposed on the obturator assembly 11 (see FIG. 1). The selective engagement between latches 19 and notches 126 enables a user to selectively lock and unlock the obturator assembly 11 to and from the cannula assembly 100.

With further regard to cover 110, FIGS. 9-14 further illustrate the features of two-piece cover 110. As discussed above, cover 110 includes a proximal housing component 110a and a distal housing component 110b. Proximal housing component 110a defines inner wall 1112 and outer wall 1114 disposed radially outwardly of the inner wall 1112. Inner wall 1112 defines central passage 1116 which is dimensioned to receive a surgical instrument.

Outer wall 1114 defines first and second annular recesses 1120, 1122 adjacent its distal end. Recesses 1120, 1122 receive corresponding structure, e.g., annular lips 1124, 1126 of distal housing component 110b to facilitate connection of the two components. As can be appreciated, proximal housing component 110a may also incorporate locking tabs which engage corresponding structure of distal housing component 110b upon relative rotation of the components 110a, 110b to securely connect the components.

More particularly, a distal portion of outer wall 1114 of proximal housing component 110a includes a pair of ramps 1200, each of which being configured to engage a threaded portion 1300 (e.g., including male threads) and/or annular lips 1124, 1126 of distal housing component 110b. Thus coupling of proximal housing component 110a and distal housing component 110b is thereby affected through alignment and rotation of the components. Additionally, proximal housing component 110a includes a stop 1210 adjacent each ramp 1200, which limits the rotational movement of distal housing component 110b with respect to proximal housing component 110a.

In order to prevent inadvertent relative rotation and thus potential decoupling of proximal housing component 1110a and distal housing component 110b, the present disclosure includes a rotation prevention mechanism 1500.

In general, the rotation prevention mechanism 1500 is a mechanism that may prevent inadvertent relative rotation, and thus potential decoupling, of proximal housing component 110a and distal housing component 110b. In disclosed embodiments, the rotation prevention mechanism 1500 may include components that are integrally formed with one or both of the proximal housing component 110a and the distal housing component 110b. Additionally or alternatively, the rotation prevention mechanism 1500 may include components that are integrally formed with components that are fixedly connected to one or both of the proximal housing component 110a and the distal housing component 110b.

The embodiment shown and described herein in FIGS. 9-14 provides an example of the rotation prevention mechanism 1500 which includes a first component that is integrally formed with the proximal housing component 110a and a second component that is fixedly connected to the distal housing component 110b. Alternate embodiments may include different arrangements, e.g., wherein the rotation prevention mechanism 1500 includes components that are integrally formed with different components that are fixedly connected to either the proximal housing component 110a and the distal housing component 110b. It should also be recognized that, while the example embodiment shown and discussed herein provides for an arrangement in which the rotation prevention mechanism 1500 includes two components, other embodiments are envisioned in which the rotation prevention mechanism 1500 includes only one component (e.g., a component that is part of or connected to a single one of the proximal housing component 110a and the distal housing component 110b), or includes more than two components (e.g., components that are part of or connected to other components in addition to the proximal housing component 110a and the distal housing component 110b).

Figure 21:
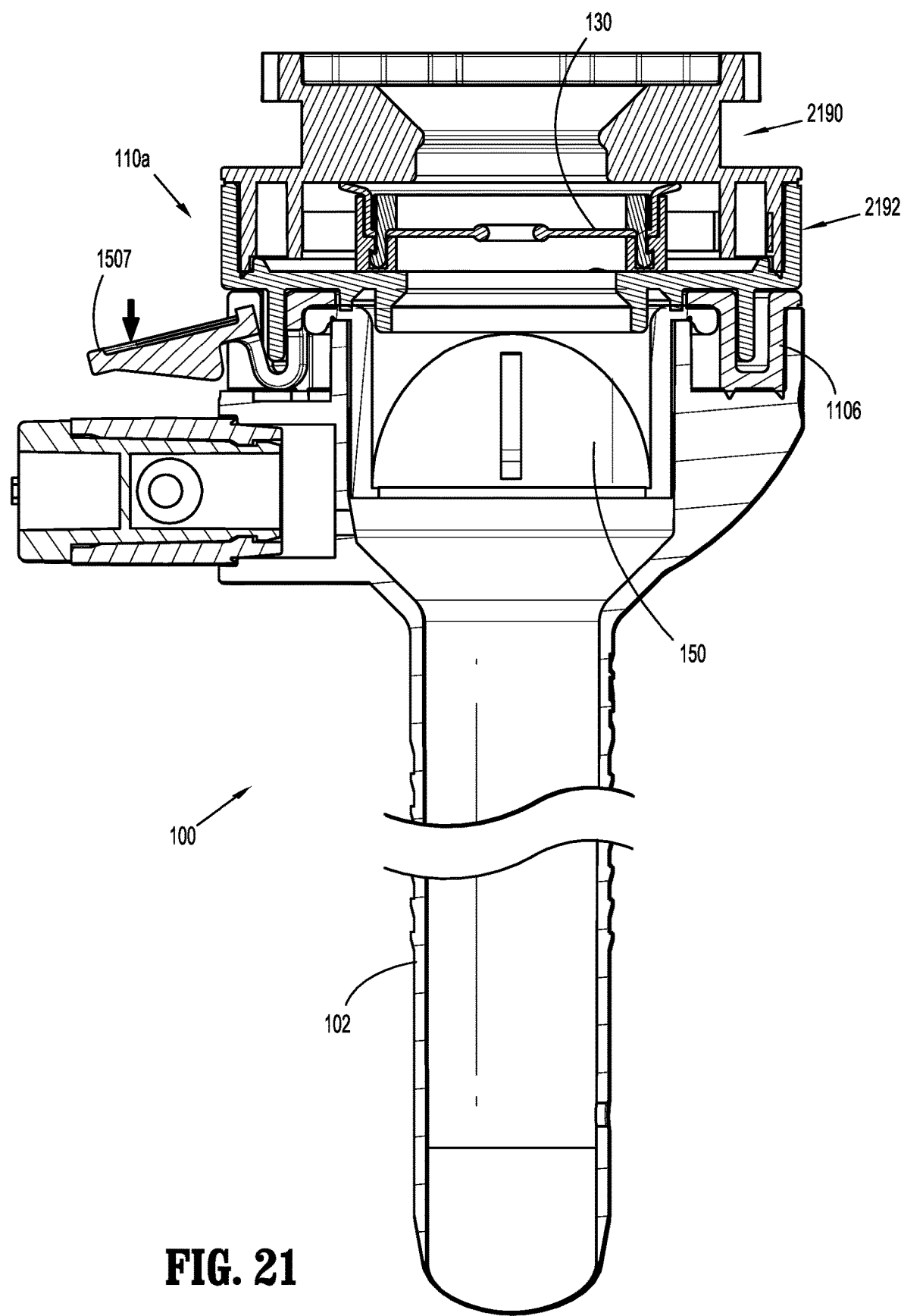
FIG. 21 is a cross-sectional view of the cannula assembly illustrating the tab in a second position.
Figure 22:
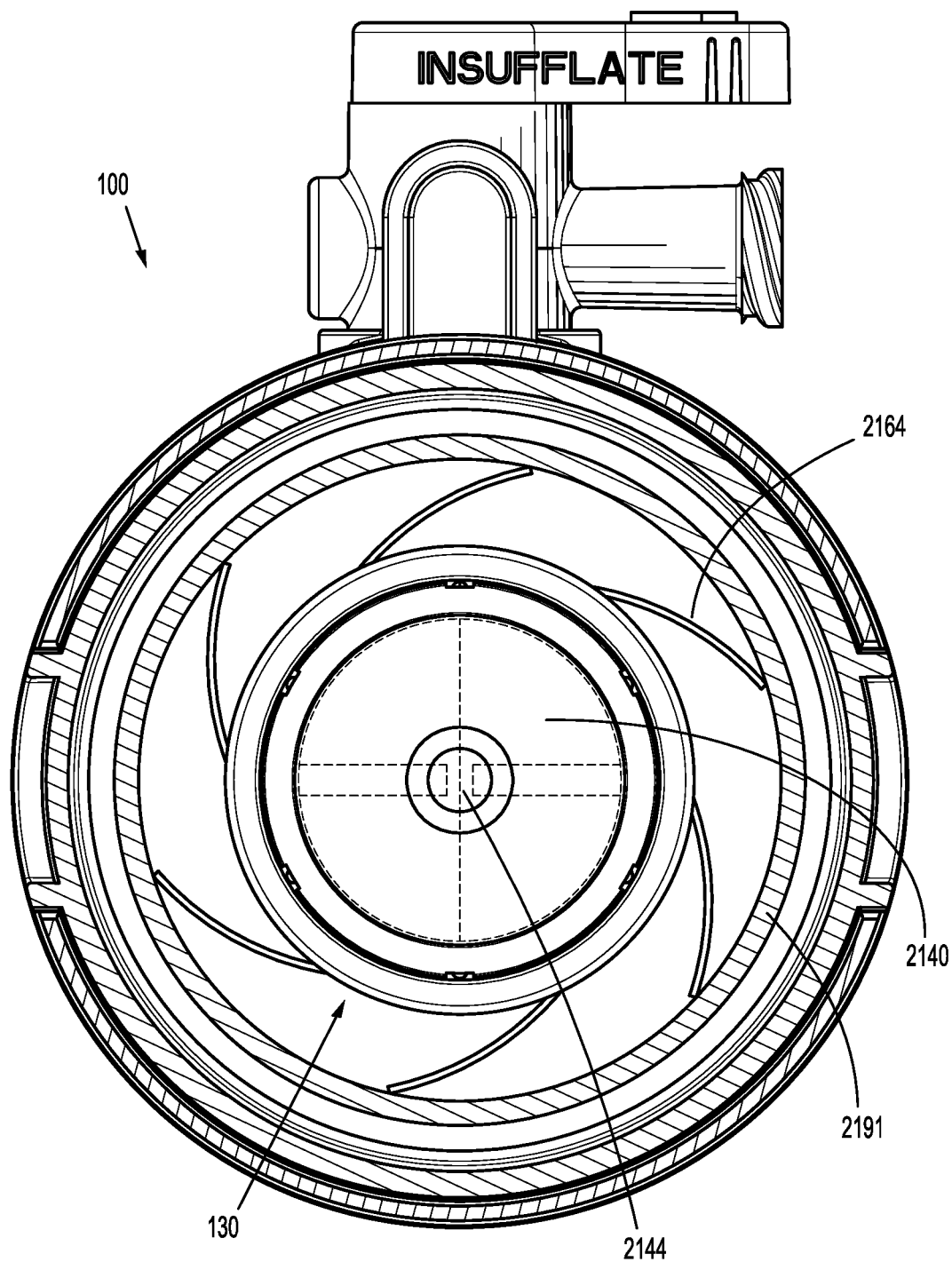
FIG. 22 is a cross-sectional view of a portion of the cannula assembly illustrating the seal assembly radially centered within the housing.

Referring now to FIGS. 9-14, there is shown an example embodiment of the rotation prevention mechanism 1500 which includes a first component 1502 and a second component 1508. As shown, the first component 1502 consists of a finger 1503 that is integrally formed with a circumferential edge of the proximal housing component 110a. In addition, as shown in this embodiment, the second component 1508 of the rotation prevention mechanism 1500 is a tab 1507 that is integrally formed with a circumferential edge of the distal housing component 110b. Tab 1507 includes a radially outward user-actuatable portion 1508 and a radially-inward locking portion 1509. The tab 1507 is configured for resilient movement relative to the distal housing component 110b about its point of attachment thereto, such that at least a portion of the tab 1507, e.g., the user-actuatable portion 1508, is moveable distally relative to the circumferential edge of the distal housing component 110b (see FIG. 21, for example).

Figure 12:
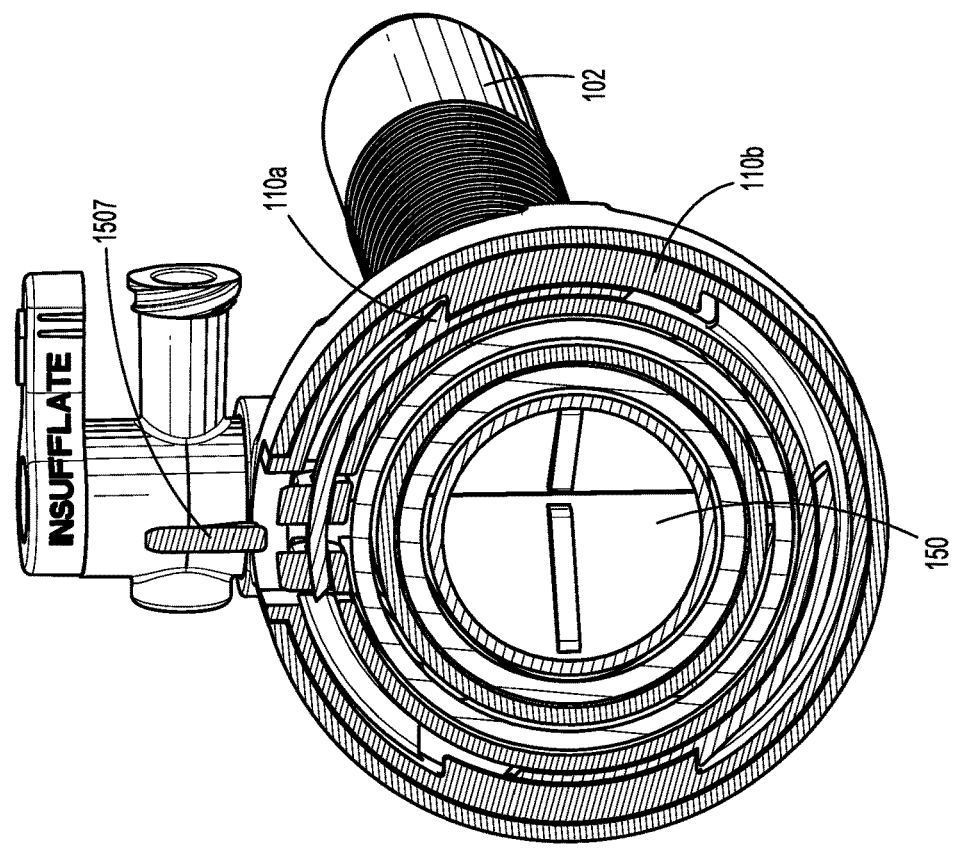
FIG. 12 is a cut-away perspective view taken along line 12-12 in FIG. 20.
Figure 13:
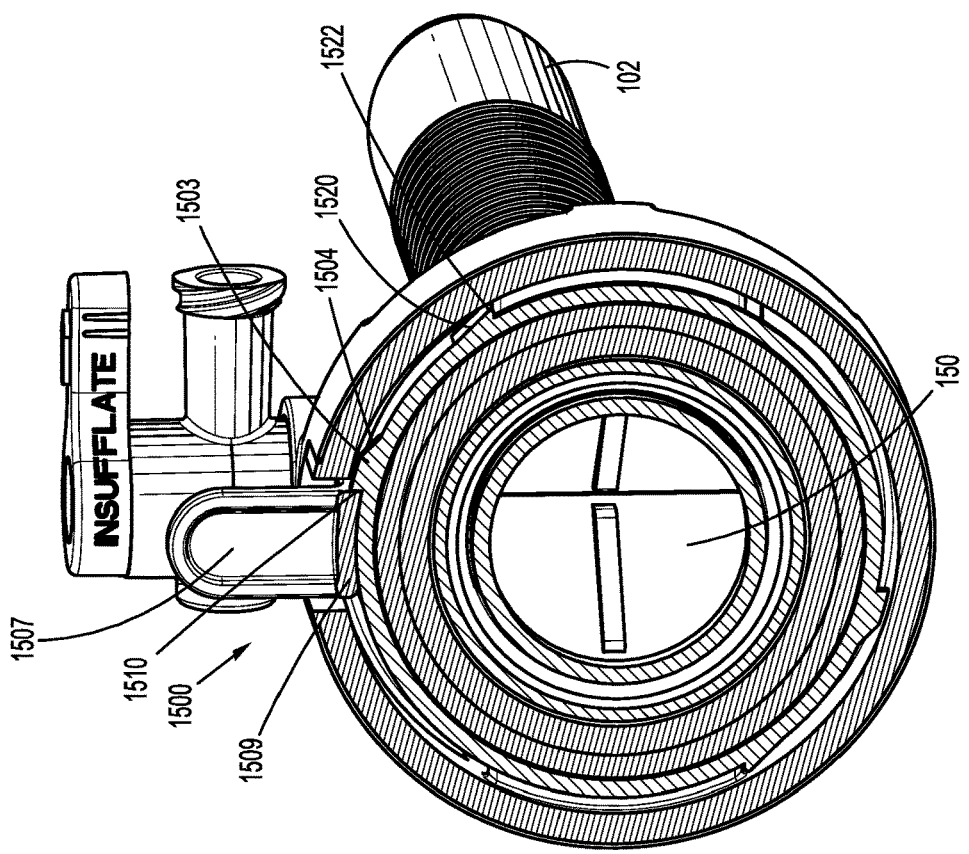
FIG. 13 is a cut-away perspective view taken along line 13-13 in FIG. 20.
Figure 14:
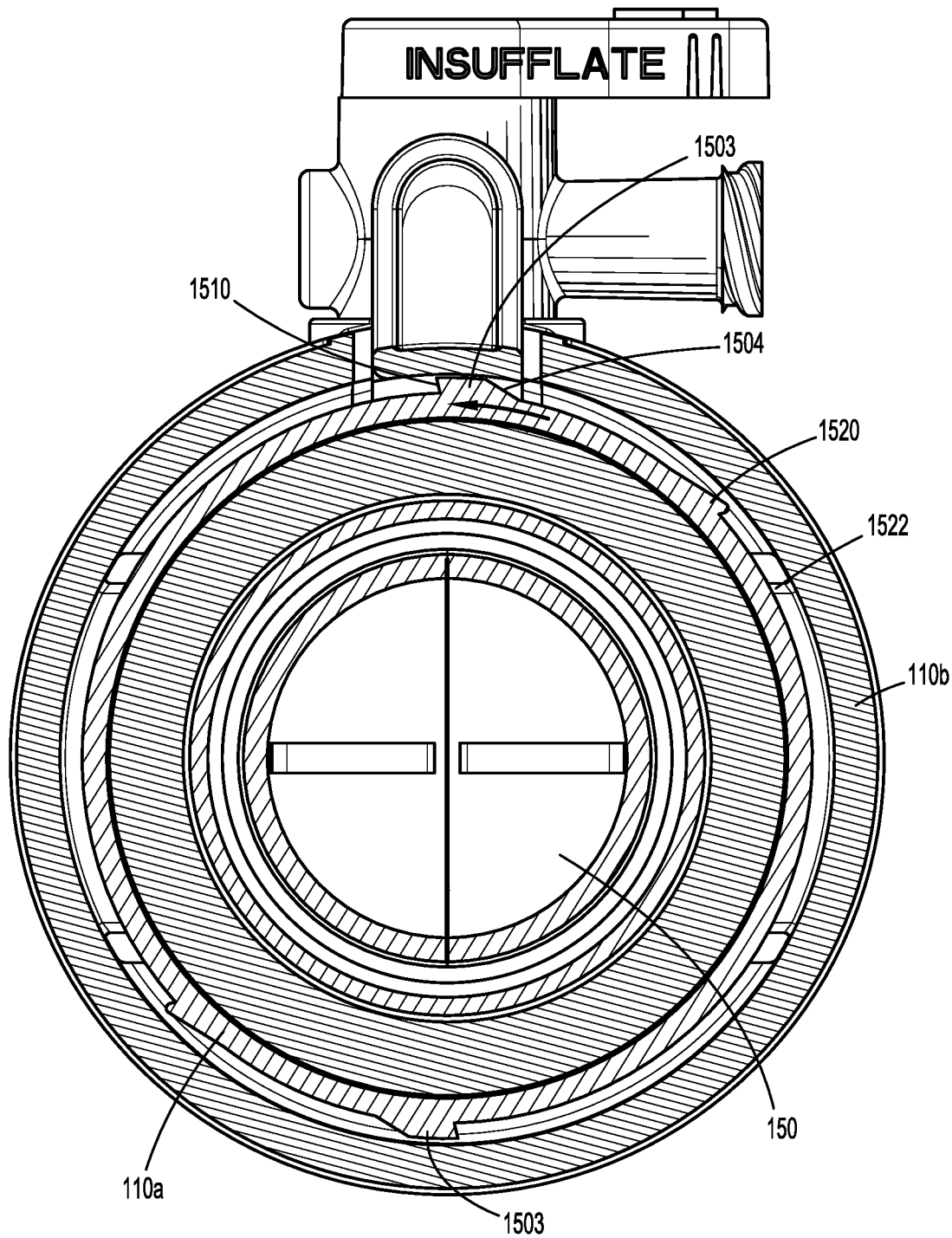
FIG. 14 is a cross-sectional view of a portion of the cannula assembly illustrating a portion of the proximal housing component engaging a portion of the distal housing component.

In this way, as the proximal housing component 110a is rotated in a first direction (e.g., clockwise when FIGS. 12 and 14 are viewed from above), a ramped surface 1504 of finger 1503 engages locking portion 1509 of tab 1507. Continued rotation of proximal housing component 110a causes finger 1503 to exert a force, e.g., a force directed in the radially outward direction, on locking portion 1509 of tab 1507. The radially outward force is sufficient to cause tab 1507 to move radially outward relative to the circumferential edge of the distal housing component 110b about its point of attachment thereto, from its first, biased position towards its second position. (It is also envisioned that the radially outward force causes a portion, e.g., user actuatable portion 1508, of tab 1507 to move distally). After a predetermined amount of rotation of the proximal housing component 110a, the finger 1503 passes the tab 1507, and causes the locking portion 1509 tab 1507 to move back to its first, biased position and adjacent with a substantially perpendicular surface 1510 of finger 1503. As can be appreciated with reference to FIG. 12, when tab 1507 is in its first position, proximal housing component 110a is effectively prevented from counter-clockwise rotation with respect to distal housing component 110b.

Additionally, in the illustrated embodiment, when sufficient rotation of proximal housing component 110a causes the finger 1503 to pass the tab 1507, a protrusion 1520 of the proximal housing component 110a contacts a stop 1522 of distal housing component 110b, thus effectively preventing additional clockwise rotation between the proximal housing component 110a and the distal housing component 110b. Accordingly, during the annular orientation of proximal housing component 110a and the distal housing component 110b that is illustrated in FIG. 12, both directions of rotation of the proximal housing component 110a are effectively prevented, and thus the proximal housing component 110a is rotationally fixed with respect to the distal housing component 110b.

In this manner, the rotation prevention mechanism 1500 automatically prevents the proximal housing component 110a from inadvertently rotating relative to, and thus inadvertently becoming disconnected from, the distal housing component 110b once the proximal housing component 110a reaches this locked position.

Once a user determines that it would be desirable to disconnect and/or remove the proximal housing component 110a from the distal housing component 110b, the user may then exert a force, e.g., a force directed in the distal direction, on the tab 1507. This distally-directed force may be sufficient to cause the user actuatable portion 1508 the tab 1507 to move distally relative to the circumferential edge of the distal housing component 110b about its point of attachment thereto until the locking portion 1509 of tab 1507 is located radially outward of finger 1503. In this position, the proximal housing component 110a is no longer prevented from rotating, but rather is free to rotate, in a second direction (i.e., counter-clockwise when FIGS. 12 and 14 are viewed from above) relative to the distal housing component 110b. In this manner, the rotation prevention mechanism 1500 provides a selectively actuatable mechanism that, when actuated, enables a user to rotate and thereby disconnect proximal housing component 110a from distal housing component 110b. It is envisioned that upon or during removal of obturator assembly 11 from tissue, a user may desire to disconnect proximal housing component 110a from distal housing component 110b to allow the obturator assembly 11 to be fully removed from the elongated portion 102 of the cannula assembly 100 without coming out of engagement with the insert seal assembly 130, for example. Further details of the cover 110 and the rotation prevention mechanism 1500 are disclosed in U.S. patent application Ser. No. 13/933,344, filed on Jul. 2, 2013, now U.S. Pat. No. 9,247,956, the entire contents of which being incorporated by reference herein.

Figure 19:
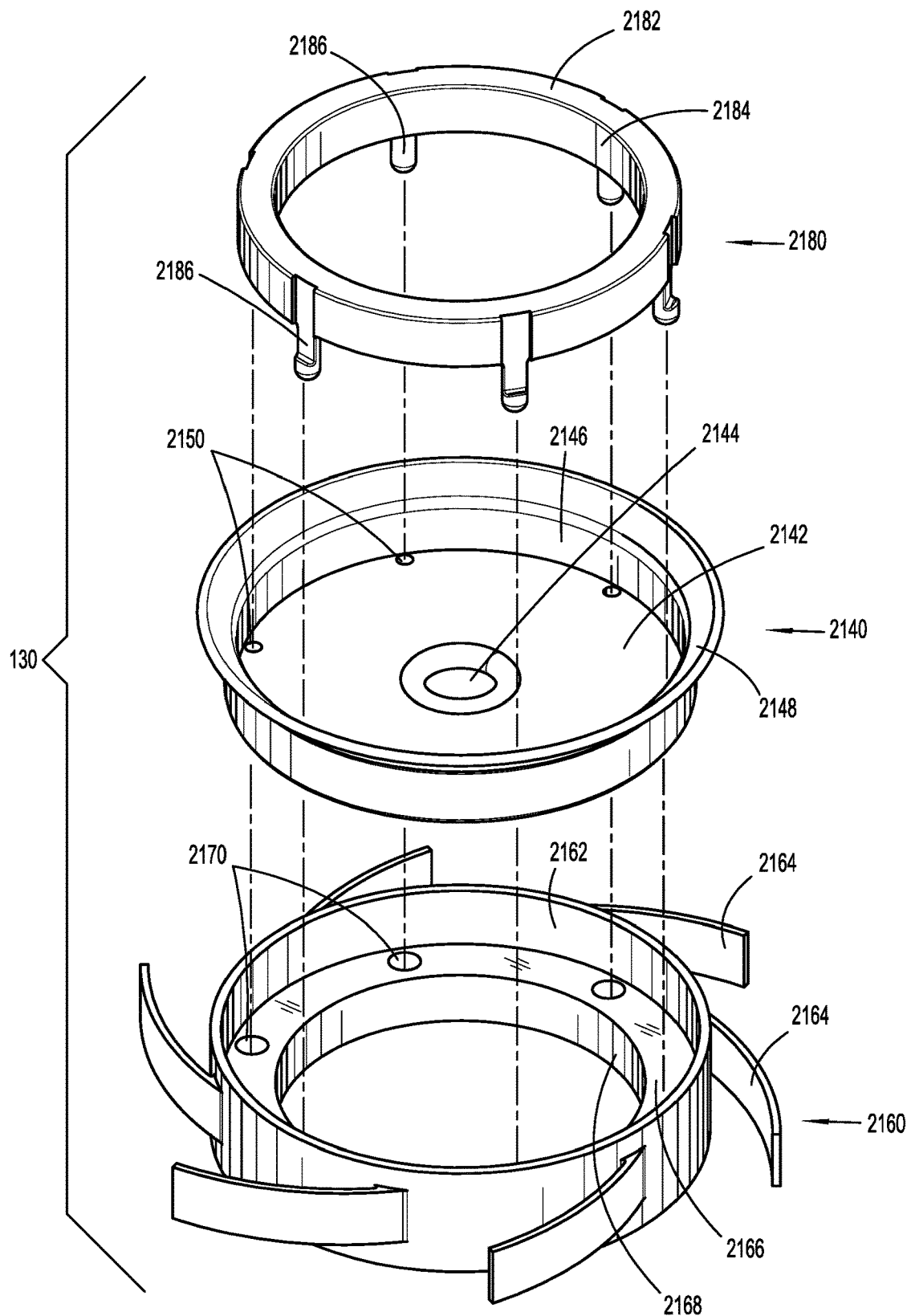
FIG. 19 is a perspective view with parts separated of the seal assembly.
Figure 20:
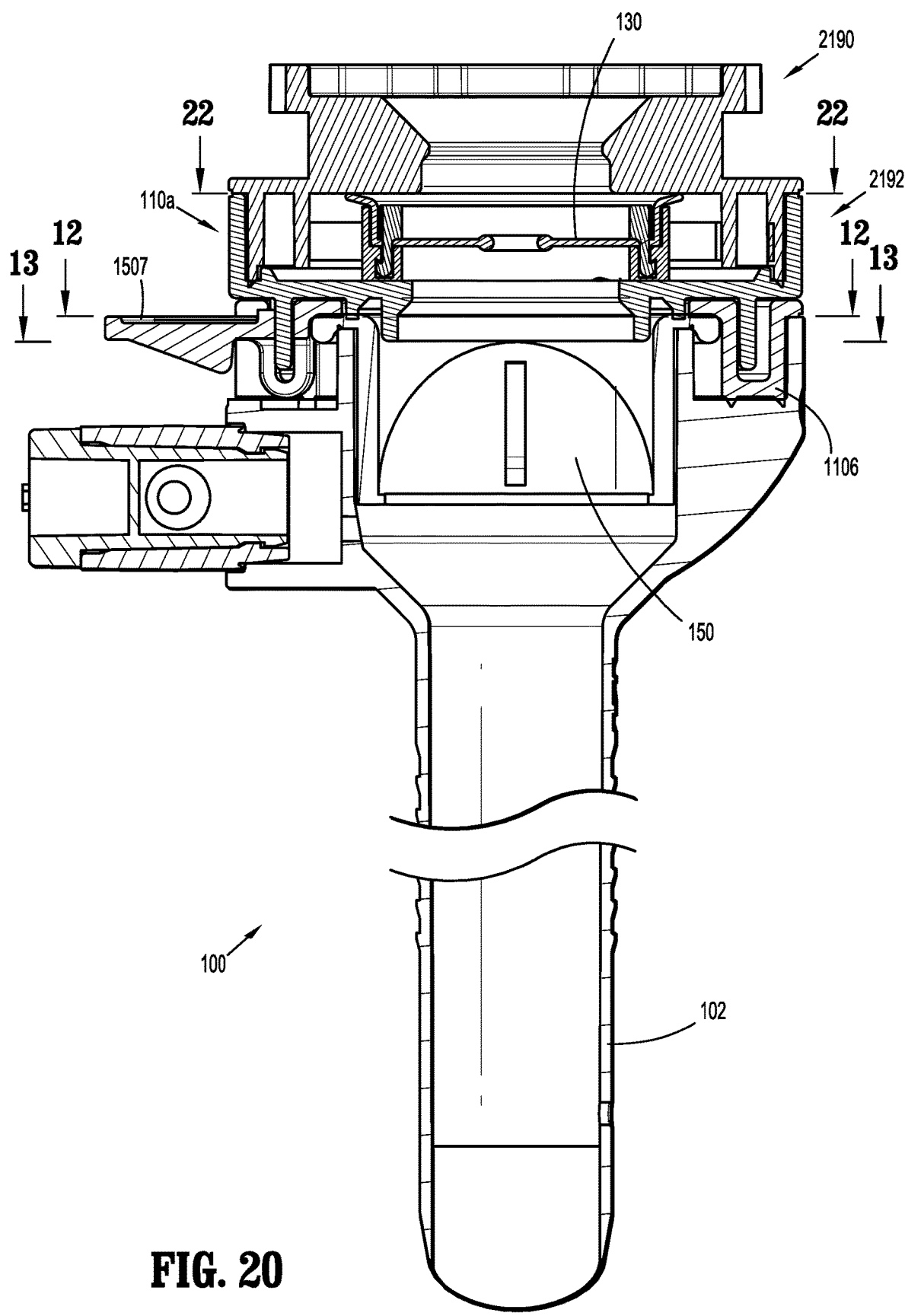
FIG. 20 is a cross-sectional view of the cannula assembly illustrating the tab in a first position.

With reference to FIGS. 15-19, and with particular reference to FIG. 19, the insert seal assembly 130 includes an elastomeric septum seal 2140, a lower seal support 2160 and an upper seal support 2180. Septum seal 2140, which is configured to provide a seal around the outer surface of an instrument passing therethrough, includes a flat seal portion 2142 having an orifice 2144 at or near its radial center, an annular wall 2146, and a peripheral seal 2148. Septum seal 2140 also includes a plurality of apertures 2150 annularly disposed on flat seal portion 2142 adjacent annular wall 2146.

Lower seal support 2160 includes a substantially vertical collar portion 2162, a plurality of spring elements or spokes 2164 extending radially outwardly from collar portion 2162, a substantially horizontal or engagement surface 2166 extending radially inward from collar portion 2162, and an inner ring 2168 extending downwardly from an inner circumference of horizontal surface 2166. Horizontal surface 2166 includes a plurality of apertures 2170 annularly disposed therearound. When insert seal assembly 130 is assembled, apertures 2170 are longitudinally aligned with apertures 2150 of septum seal 2140.

Upper seal support 2180 includes a ring-like, substantially horizontal surface 2182, an annular, substantially vertical wall 2184 depending downwardly from surface 2182, and a plurality of fingers 2186 extending downwardly from wall 2184. Fingers 2186, apertures 2150 of septum seal 2140, and apertures 2170 of lower seal support 2160 are longitudinally aligned, such that when insert seal assembly 130 is assembled, fingers 2186 extend through apertures 2150 of septum seal 2140 and through apertures 2170 of lower seal support 2160. Further, this engagement between fingers 2186, apertures 2150 of septum seal 2140, and apertures 2170 of lower seal support 2160 helps secure the three components together and helps prevent relative movement along and about the longitudinal axis B-B.

Figure 15:
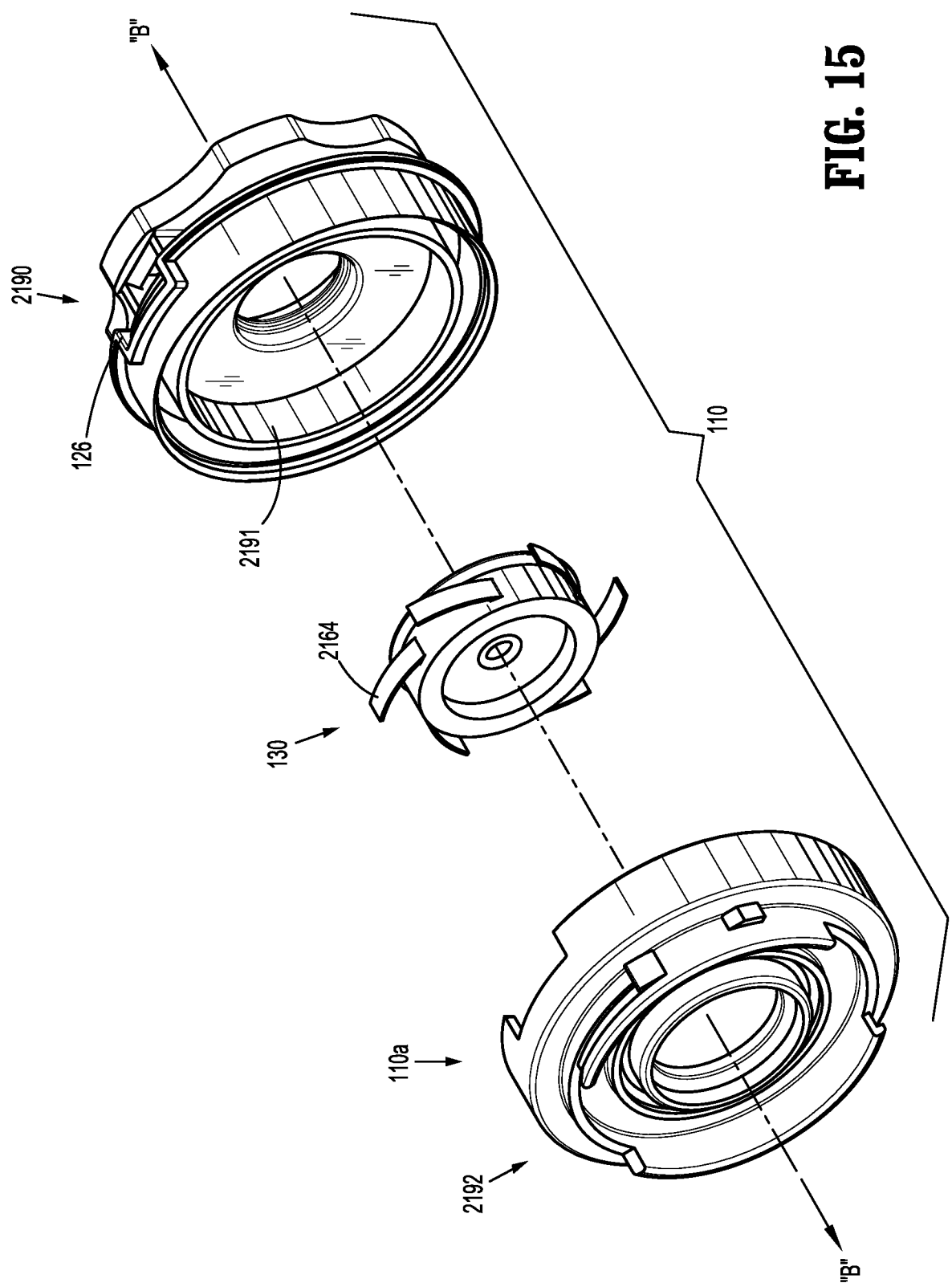
FIG. 15 is a perspective, assembly view of the seal assembly and a portion of the housing.
Figure 16:
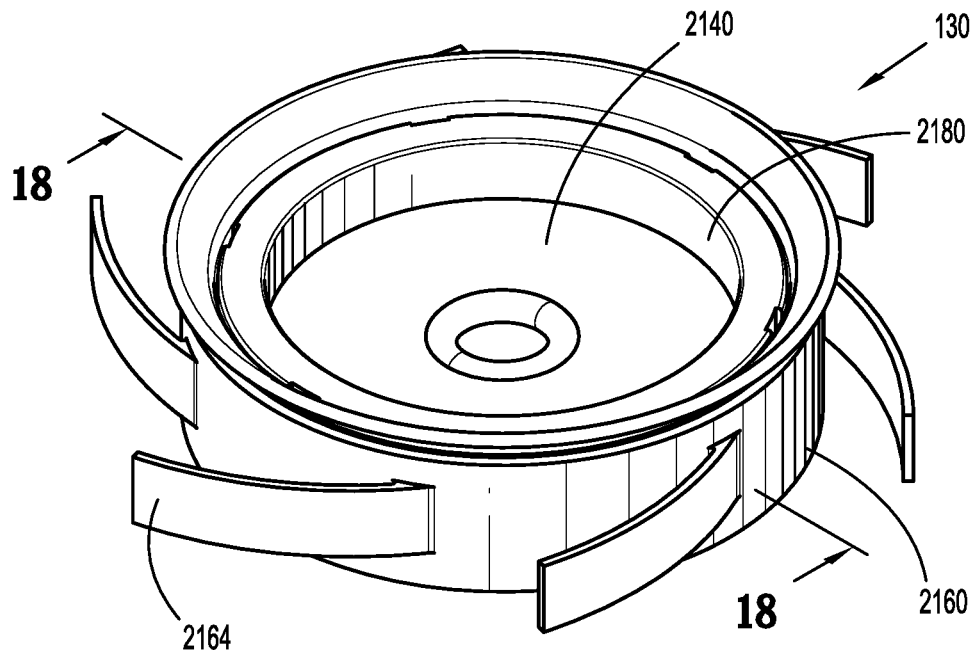
FIG. 16 is a perspective view of the seal assembly.
Figure 17:
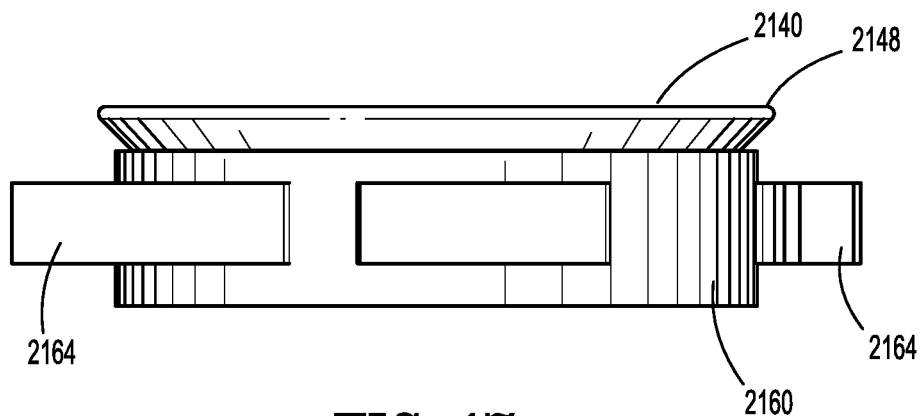
FIG. 17 is a side view of the seal assembly.
Figure 18:
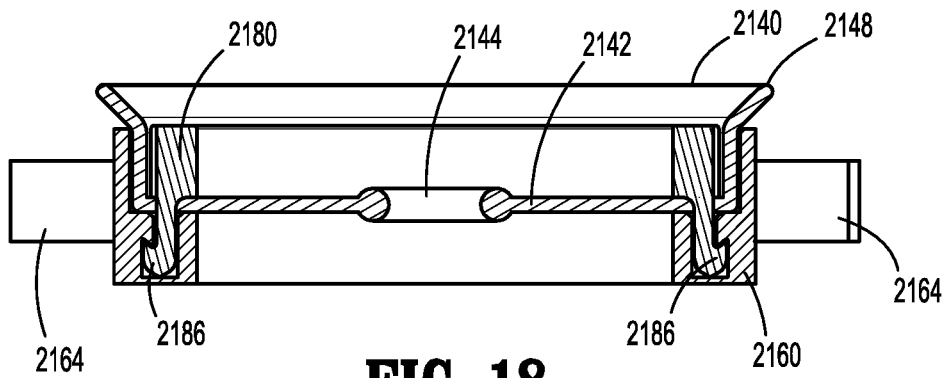
FIG. 18 is a cross-sectional view of the seal assembly taken along line 18-18 in FIG. 16.

With particular reference to FIG. 15, after assembly of insert seal assembly 130, insert seal assembly 130 is positioned within a portion of cover 110. In particular, insert seal assembly 130 is housed within proximal housing component 110a. Further, and with continued reference to FIG. 15 and with additional reference to FIGS. 20-23, insert seal assembly 130 is positioned between a first portion 2190 and a second portion 2192 of proximal housing component 110a, and is radially movable therein. First portion 2190 and second portion 2192 of proximal housing component 110a are selectively engageable with each other (e.g., via a snap-fit arrangement). Further, at least one spoke 2164 is in contact with an inner wall 2191 of first portion 2190. Spokes 2164 are configured to help maintain orifice 2144 at or near the radial center within proximal housing component 110a, and to help prevent free lateral movement of septum seal 2140 within proximal housing component 110a. That is, spokes 2164 of lower seal support 2160 bias insert seal assembly 130 toward the radial center of proximal housing component 110a.

Figure 23:
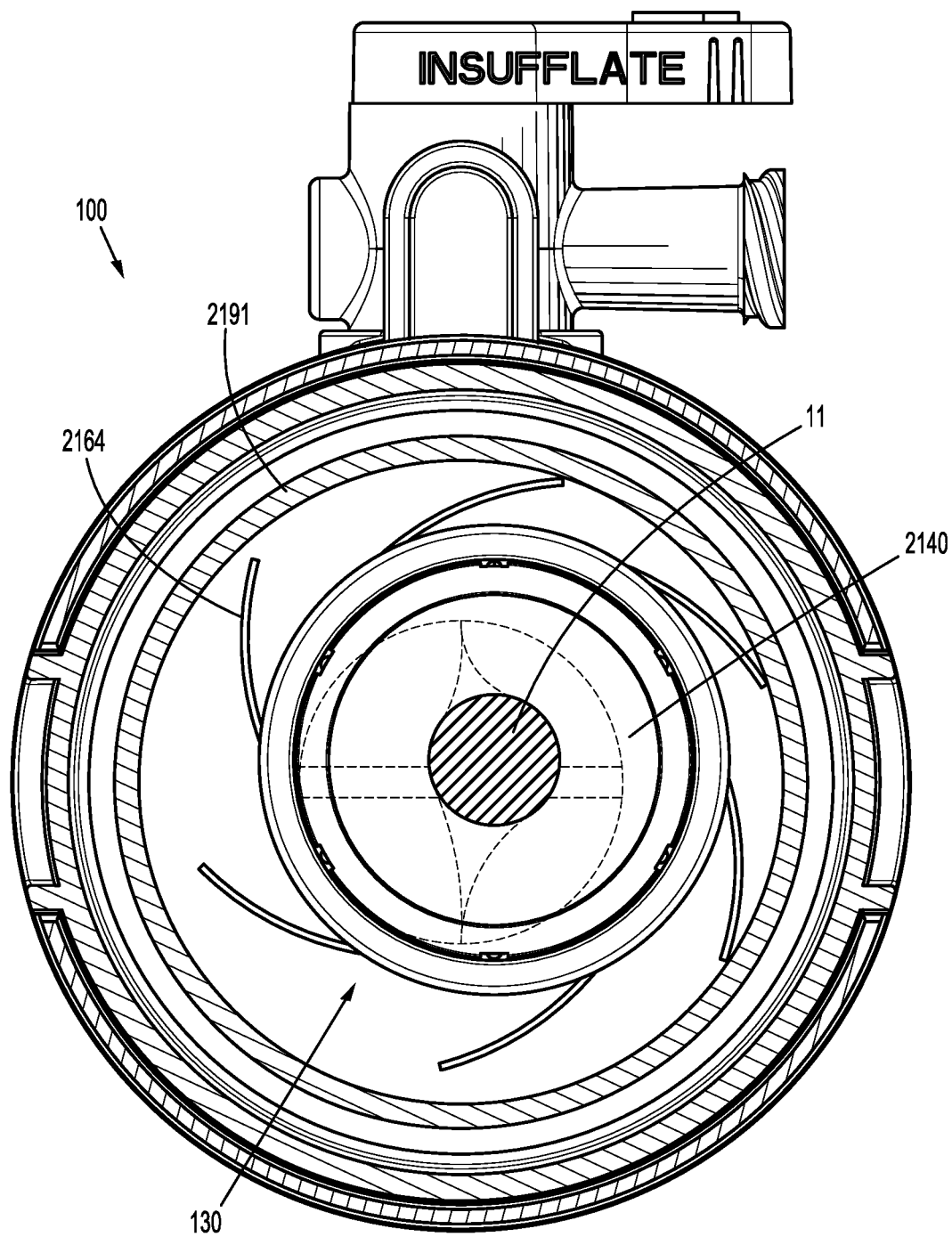
FIG. 23 is a cross-sectional view of a portion of the cannula assembly illustrating an instrument inserted through the seal assembly, and the seal assembly being radially offset within the housing.

Thus, upon removal of obturator assembly 11 from the cannula assembly 100, the orifice 2144 of the septum seal 2140, which may otherwise move to an off-center location (as shown in FIG. 23), is urged toward the radial center of proximal housing component 110a, such that orifice 2144 is in a centered location for reception of a subsequently-inserted surgical instrument (e.g., a surgical stapling device).

Figure 29:
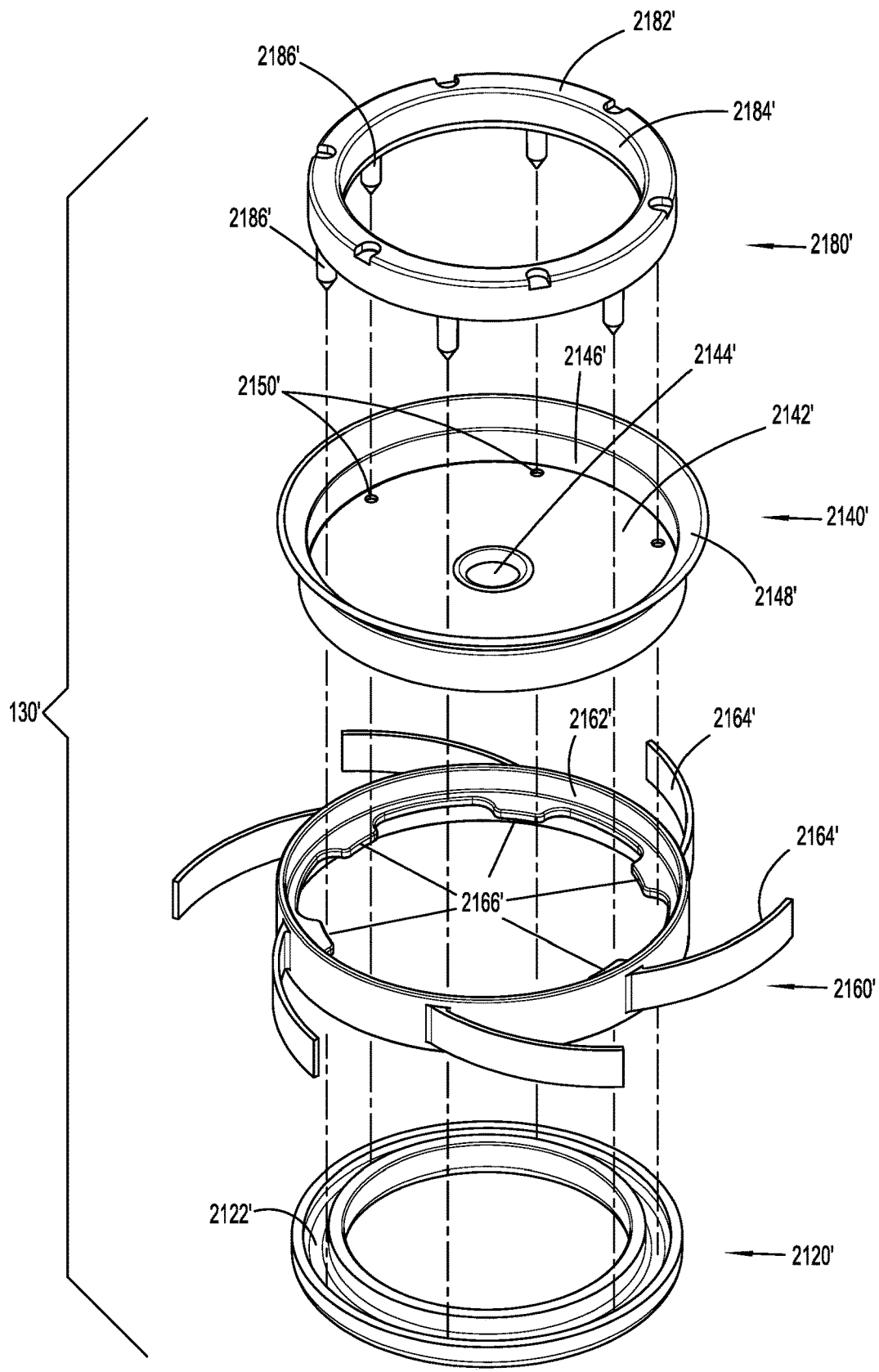
FIG. 29 is a perspective view with parts separated of the seal assembly of FIG. 25.

With reference to FIGS. 25-29, another embodiment of insert seal assembly 130' is shown. With particular reference to FIG. 29, the insert seal assembly 130' includes an elastomeric septum seal 2140', a return spring 2160', a lower seal retainer 2120', and an upper seal retainer 2180'. Septum seal 2140', which is configured to provide a seal around the outer surface of an instrument passing therethrough, includes a flat seal portion 2142' having an orifice 2144' at or near its radial center, an annular wall 2146', and a peripheral seal 2148'. Septum seal 2140' also includes a plurality of apertures 2150' annularly disposed on flat seal portion 2142' adjacent annular wall 2146'.

The return spring 2160' includes a substantially vertical collar portion 2162' and a plurality of spring elements or spokes 2164' extending radially outwardly from the collar portion 2162'. Additionally, the return spring 2160' includes a plurality of spaced apart protrusions 2166' that extend from the vertical collar portion 2162' towards the center of the return spring 2160'. The plurality of spaced apart protrusions 2160' are sandwiched between the lower seal retainer 2120' and the upper seal retainer 2180', as shown in the assembled view of FIG. 28. By sandwiching the plurality of spaced apart protrusions 2160' between the lower seal retainer 2120' and the upper seal retainer 2180', the return spring 2160' is more stable relative to the lower seal retainer 2120' and the upper seal retainer 2180' during use and less likely to be dislodged when the movement of an instrument within the aperture 2144' causes the insert seal assembly 130' to move within proximal housing component 110a.

Upper seal support 2180' includes a ring-like, substantially horizontal surface 2182', an annular, substantially vertical wall 2184' depending downwardly from surface 2182', and a plurality of fingers 2186' extending downwardly from wall 2184'. Fingers 2186' and apertures 2150' of septum seal 2140' are longitudinally aligned, such that when insert seal assembly 130' is assembled, fingers 2186' extend through apertures 2150' of septum seal 2140'. Further, this engagement between fingers 2186' and apertures 2150' of septum seal 2140' assists in securing the two components together and helps prevent relative movement along and about the longitudinal axis B-B. Additionally, the engagement of fingers 2186' with apertures 2150' aligns upper seal support 2180' with septum seal 2140'. Each protrusion 2166' of return spring 2160' is located between corresponding fingers 2186' for limiting relative rotation between upper seal support 2180', septum seal 2140', and return spring 2160' (see FIG. 29). Alternatively, each finger 2186' frictionally engages a corresponding protrusion 2166' for securing the relative rotational positions between the return spring 2160', the septum seal 2140', and the upper seal support 2180'.

Figure 25:
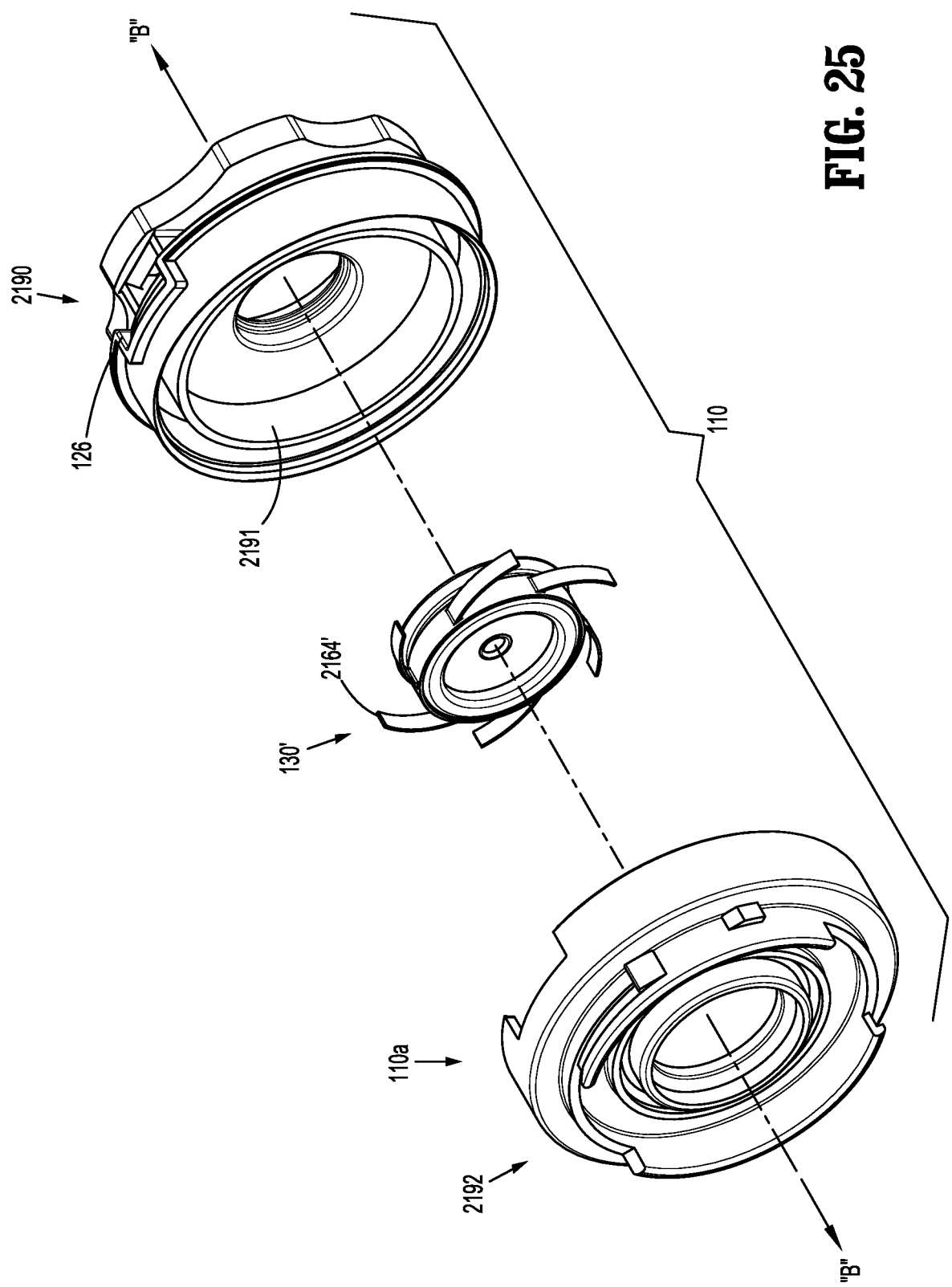
FIG. 25 is a perspective, assembly view of a seal assembly and a portion of the housing in accordance with embodiments of the present disclosure.
Figure 26:
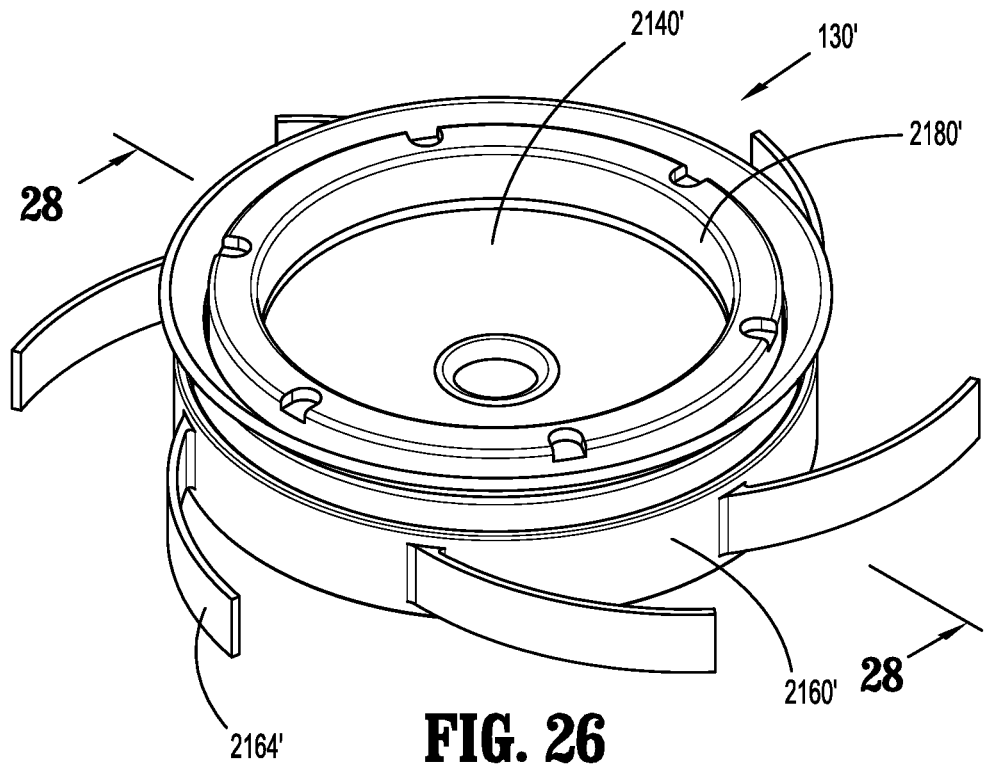
FIG. 26 is a perspective view of the seal assembly of FIG. 25.
Figure 27:
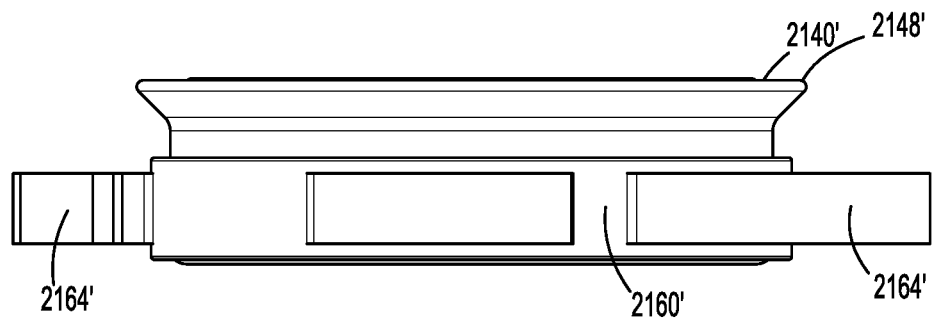
FIG. 27 is a side view of the seal assembly of FIG. 25.
Figure 28:
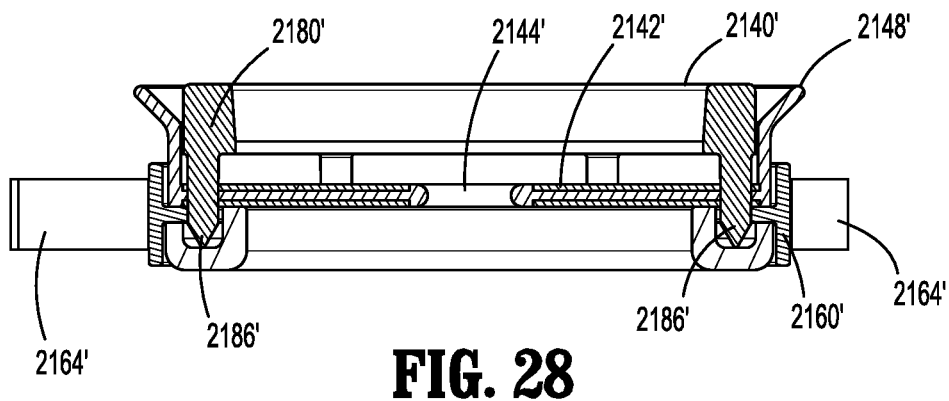
FIG. 28 is a cross-sectional view of the seal assembly of FIG. 25 taken along line 28-28 in FIG. 26.

With particular reference to FIG. 25, after assembly of insert seal assembly 130', insert seal assembly 130' is positioned within a portion of cover 110. Further details regarding positioning, use and function of insert seal assembly 130' are similar to the positioning, use and function of insert seal assembly 130, as discussed above. Additionally, and as can be appreciated, the apparatuses disclosed herein can include either insert seal assembly 130 or insert seal assembly 130'.

The use and function of the system 10 will now be discussed. In embodiments, in laparoscopic surgery, the abdominal cavity is insufflated with a suitable biocompatible gas such as, e.g., $CO_2$ gas, to insufflate the body cavity and lift the body cavity wall away from the internal organs therein. The insufflation may be performed with an insufflation needle or similar device as is conventional in the art. In alternative embodiments, the system 10 may also be utilized in a space that has not been insufflated.

Figure 24:
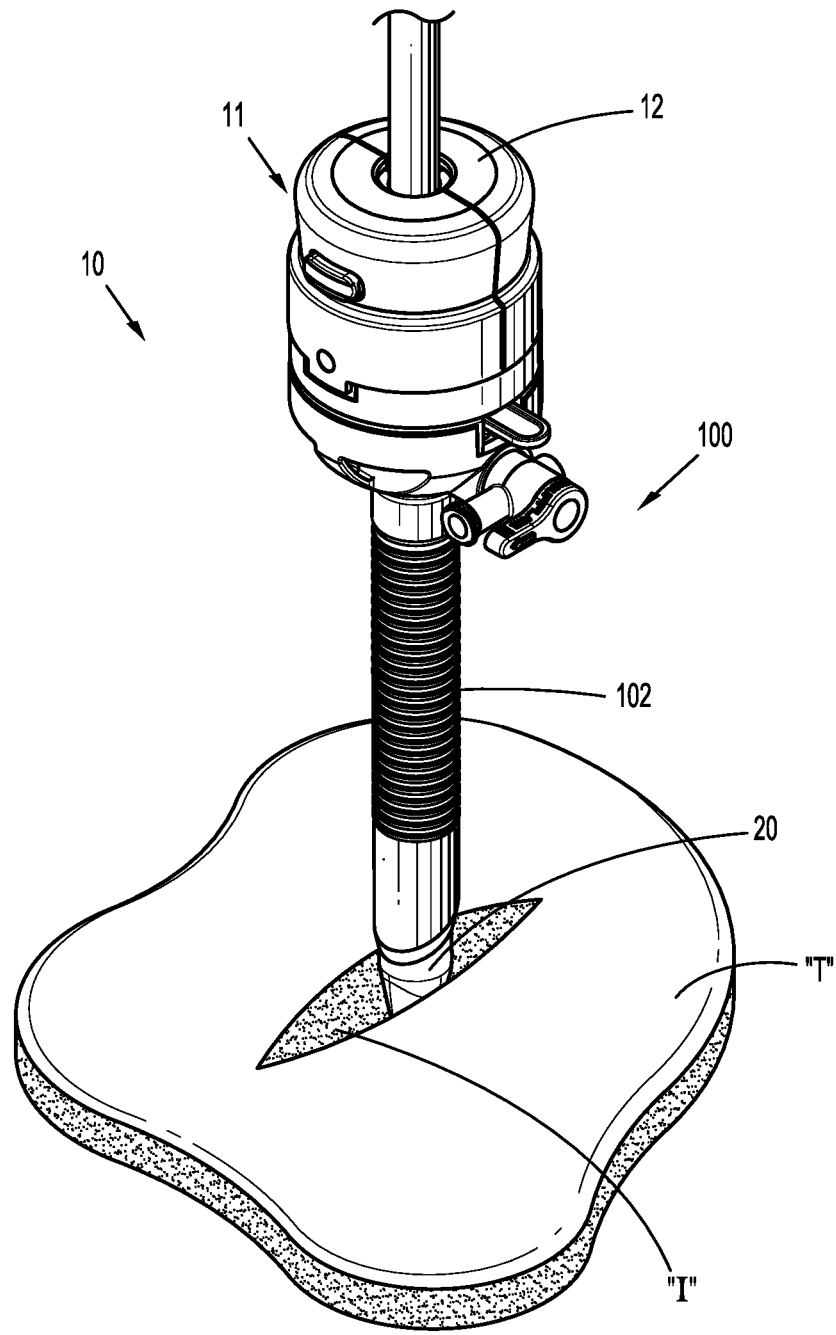
FIG. 24 is a perspective view illustrating an endoscope positioned within the optical access apparatus and accessing body tissue.

In use, an initial incision "I" is made in tissue "T" (e.g., skin) by a surgical instrument (e.g., a scalpel) (see FIG. 24). The incision "I" is preferably small, for example, within a range from about 2 mm to about 7 mm. The obturator assembly 11 of the surgical visualization system 10 is at least partially introduced within the cannula assembly 100 with the obturator member 14 extending through the aperture 2144 of the septum seal 2140 and through the zero-closure seal 150. The assembled unit is positioned within the initial incision and against the target tissue, e.g., the abdominal lining. As discussed above, an endoscope may be inserted through the obturator assembly 11 such that the distal viewing end of the endoscope is positioned against the chamfered surface of the optical member 20. The endoscope may be retained at this relative position within the obturator assembly 11 by the scope retention member 170.

The optical member 20 is manipulated relative to the tissue whereby the atraumatic guiding nub 26 engages tissue and, in combination with the concave and/or convex outer surfaces 244, gently dissect or separate the tissue along a natural tissue plane to gain access to an underlying cavity in a non-traumatic fashion. During insertion, the tissue adjacent the optical member 20 is viewed with the endoscope. During advancement of system 10, the endoscope is utilized to view the path along which the system is advanced to ensure that any underlying tissue or organ site is prevented from contact with the obturator assembly 11 and also to confirm entry within the body cavity.

Once system 10 is positioned at the desired location, the endoscope may be used to monitor the desired surgical procedure being performed within the cavity. In the alternative, the endoscope may be inserted into and secured in the obturator assembly 11 after the obturator assembly 11 has been positioned within tissue. The obturator assembly 11 may then be removed from the cannula assembly 100. Instruments may be introduced within the cannula assembly 100 to perform a surgical procedure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A seal assembly for use with a surgical instrument, the seal assembly comprising:
   a return spring including a collar portion and a plurality of spokes, the plurality of spokes extending radially outward from the collar portion; and
   a septum seal engaged with the return spring, the septum seal including an annular wall, an orifice and a peripheral seal extending proximally of and in contact with a proximal edge of the collar portion of the return spring, a proximal-most edge of the peripheral seal positioned proximally of a proximal-most portion of each spoke of the plurality of spokes, the peripheral seal extending radially outwardly and proximally from an upper portion of the annular wall such that the peripheral seal and the annular wall form an obtuse angle, the orifice configured to provide a seal about a portion of an instrument inserted through the orifice,
   wherein the plurality of spokes of the return spring is configured to bias the septum seal.

2. The seal assembly according to claim 1, further including a first seal support having an engagement surface, the engagement surface contacting a portion of the septum seal and including a plurality of apertures extending through the engagement surface.

3. The seal assembly according to claim 2, wherein the septum seal includes a surface having a plurality of apertures.

4. The seal assembly according to claim 3, further including a second seal support having a plurality of fingers, each finger of the plurality of fingers extending through a corresponding aperture of the plurality of apertures of the septum seal.

5. The seal assembly according to claim 4, wherein at least a portion of the return spring is sandwiched between the first seal support and the second seal support.

6. The seal assembly according to claim 4, wherein the return spring further includes a plurality of protrusions extending radially inward from the collar portion, each protrusion of the plurality of protrusions cooperating with a corresponding finger of the plurality of fingers of the second seal support for controlling rotational movement between the return spring and the septum seal.

7. The seal assembly according to claim 1, wherein the return spring is disposed at least partially within a housing, and wherein the housing is configured to limit angulation of the septum seal with respect to the housing.

8. The seal assembly according to claim 1, wherein the annular wall extends from a planar surface.

9. The seal assembly according to claim 1, wherein the septum seal includes an annular wall and the peripheral seal extends radially outward from an upper portion of the annular wall.

10. The seal assembly according to claim 1, wherein the return spring includes a plurality of spaced apart protrusions that extend radially inward.

11. The seal assembly according to claim 1, wherein the return spring further includes a plurality of protrusions extending radially inward from the collar portion.

12. A cannula assembly comprising:
    a cannula housing; and
    a seal assembly engaged with the cannula housing, and including:
      a return member including a collar portion and a plurality of spokes, the
      plurality of spokes extending radially outward from the collar portion; and a seal positioned at least partially within the return member, the seal including an orifice, an annular wall, and a peripheral seal, the orifice configured to provide a seal about a portion of an instrument inserted through the orifice, the peripheral seal extending proximally of and in contact with a proximal edge of the collar portion of the return member, the peripheral seal extending radially outwardly and proximally from an upper portion of the annular wall such that the peripheral seal and the annular wall form an obtuse angle, wherein the plurality of spokes of the return member is configured to bias the seal toward a radial center of the cannula housing.

13. The cannula assembly according to claim 12, wherein the seal assembly further includes a first seal support including an engagement surface, the engagement surface contacting a portion of the seal and including a plurality of apertures extending through the engagement surface.

14. The cannula assembly according to claim 13, wherein the seal includes a surface having a plurality of apertures.

15. The cannula assembly according to claim 14, wherein the seal assembly further includes a second seal support including a plurality of fingers, each finger of the plurality of fingers extending through a corresponding aperture of the plurality of apertures of the seal.

16. The cannula assembly according to claim 13, wherein the return member is received at least partially within an annular channel of the first seal support.

17. The cannula assembly according to claim 12, wherein the return member includes a collar portion which contacts a wall of the seal.

* * * * *